(12) United States Patent
Sobel et al.

(10) Patent No.: US 10,204,176 B2
(45) Date of Patent: Feb. 12, 2019

(54) METHOD AND SYSTEM FOR DETERMINING OLFACTORY PERCEPTION SIGNATURE

(71) Applicant: Yeda Research and Development Co. Ltd., Rehovot (IL)

(72) Inventors: Noam Sobel, Jaffa (IL); Lavi Secundo, Rehovot (IL); Kobi Snitz, Rohovot (IL); Kineret Weissler, Rehovot (IL); Liron Pinchover, Rohovot (IL); Idan Frumin, Rehovot (IL); Dana Shoshana Bar Zvi Mildworf, Rehovot (IL); Sagit Shushan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 263 days.

(21) Appl. No.: 15/188,104

(22) Filed: Jun. 21, 2016

(65) Prior Publication Data

US 2017/0364605 A1 Dec. 21, 2017

(51) Int. Cl.
| | | |
|---|---|---|
| *A61B 5/00* | (2006.01) | |
| *G06F 17/30* | (2006.01) | |
| *G06F 19/00* | (2018.01) | |
| *G16H 10/20* | (2018.01) | |

(52) U.S. Cl.
CPC ...... *G06F 17/30979* (2013.01); *A61B 5/4011* (2013.01); *G06F 19/00* (2013.01); *G16H 10/20* (2018.01); *A61B 2503/12* (2013.01)

(58) Field of Classification Search
CPC ............ G06F 17/30979; A61B 5/4011; A61B 2503/12

USPC ........ 73/23.34, 865.7; 700/266; 702/22, 24, 702/31, 32, 127, 189, 198; 705/500

See application file for complete search history.

(56) References Cited

U.S. PATENT DOCUMENTS 6,558,322 B1 5/2003 Busch

OTHER PUBLICATIONS

Khan et al. "Predicting Odor Pleasantness From Odorant Structure: Pleasantness as a Reflection of the Physical World", the Journal of Neuroscience, 27(37): 10015-10023, Sep. 12, 2007.
Milinski et al. "Evidence for MHC-Correlated Perfume Preferences in Humans", Behavioral Ecology, 12(2): 140-149, Mar. 1, 2001.
Wise et al. "Quantification of Odor Quality", Chemical Senses, 25(4): 429-443, Aug. 1, 2000.

*Primary Examiner* — Robert R Raevis

(57) ABSTRACT

A method of determining olfactory perception signature of a subject is disclosed. The method comprises: providing the subject with a plurality of physical odorant samples for sniffing; for each sniffed odorant sample, presenting to the subject, by a user interface, a set of odorant descriptors and a respective set of rating controls, and receiving ratings entered by the subject using the rating controls. Each rating is indicative of a descriptiveness of a respective odorant descriptor for the odorant sample, thereby obtaining a set of descriptiveness levels for the odorant sample. The method also comprises calculating, by a computer, relations between pairs of sets of descriptiveness levels corresponding to pairs of odorant samples, to provide a vector of relations, wherein the vector represents the olfactory perception signature of the subject.

23 Claims, 15 Drawing Sheets
(11 of 15 Drawing Sheet(s) Filed in Color)

FIG. 1B

John's olfactory fingerprint = [43.65, 50.21, 53.71]
Jane's olfactory fingerprint = [25.12, 30.74, 11.23]
Pete's olfactory fingerprint = [88.62, 34.73, 28.24]

John's match to Jane: corr([43.65, 50.21, 53.71], [25.12, 30.74, 11.23]) = -0.56
John's match to Pete: corr([43.65, 50.21, 53.71], [88.62, 34.73, 28.24]) = -0.97
Jane's match to Pete: corr([25.12, 30.74, 11.23], [88.62, 34.73, 28.24]) = 0.33

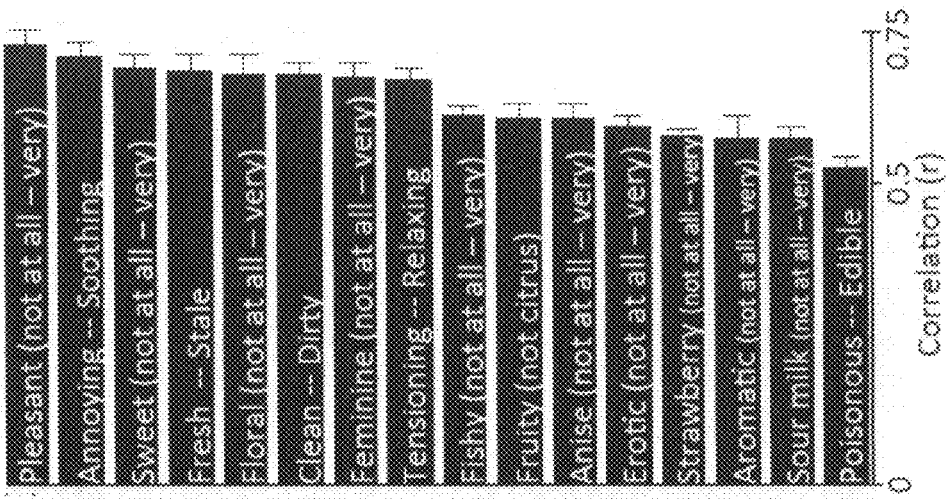
FIG. 2A  FIG. 2B
FIG. 2C  FIG. 2D
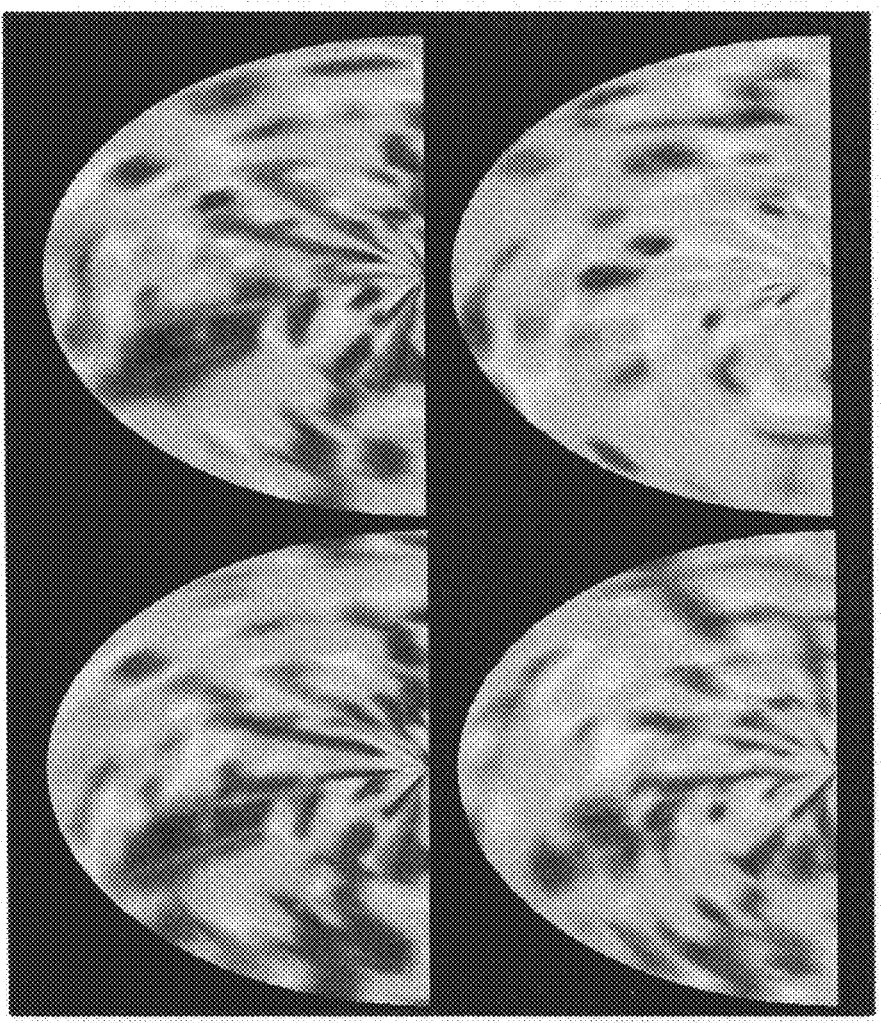
FIG. 2E

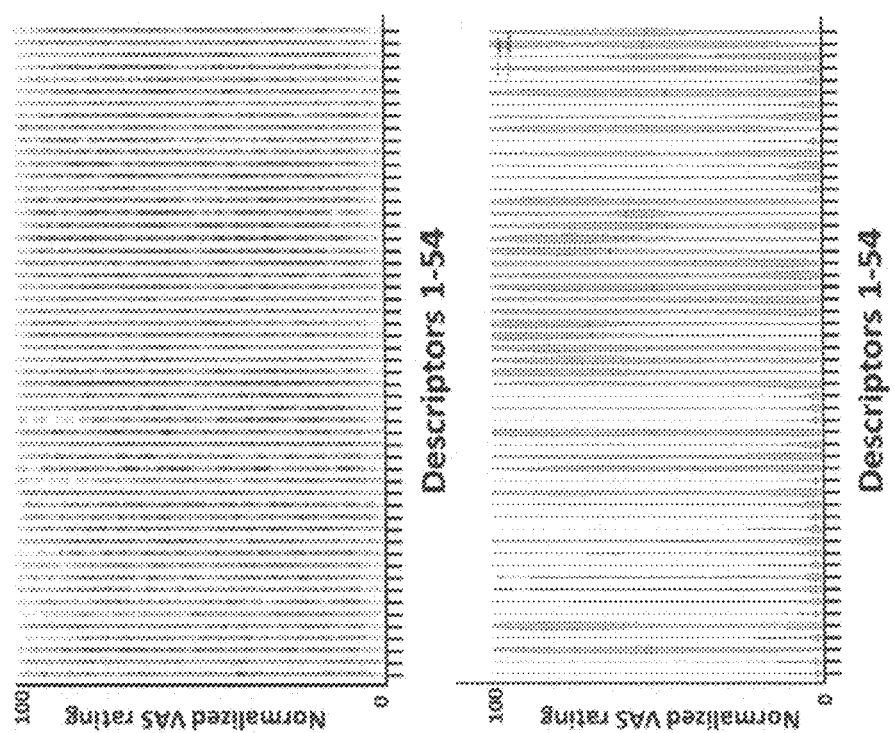

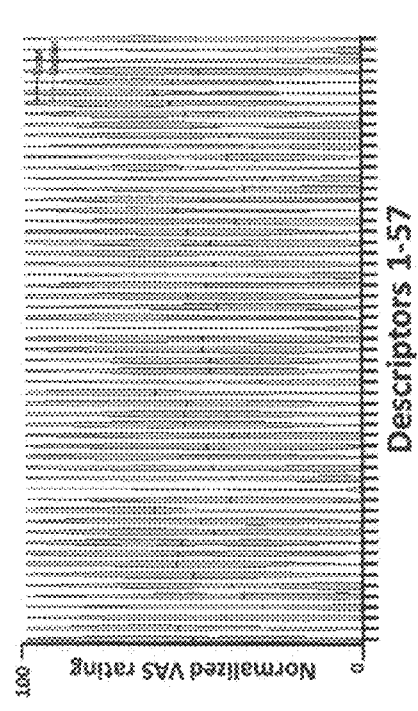
FIG. 7A
FIG. 7B

One subject's correlation coefficients

Distribution of correlation coefficients

PERMANOVA Pseudo F, same session

PERMANOVA Pseudo F, different sessions

HLA Match

One subject's correlation coefficients

Distribution of correlation coefficients

PERMANOVA Pseudo F, same session

PERMANOVA Pseudo F, different sessions

HLA Match

One subject's correlation coefficients

Distribution of correlation coefficients

PERMANOVA Pseudo F, same session

PERMANOVA Pseudo F, different sessions

HLA Match

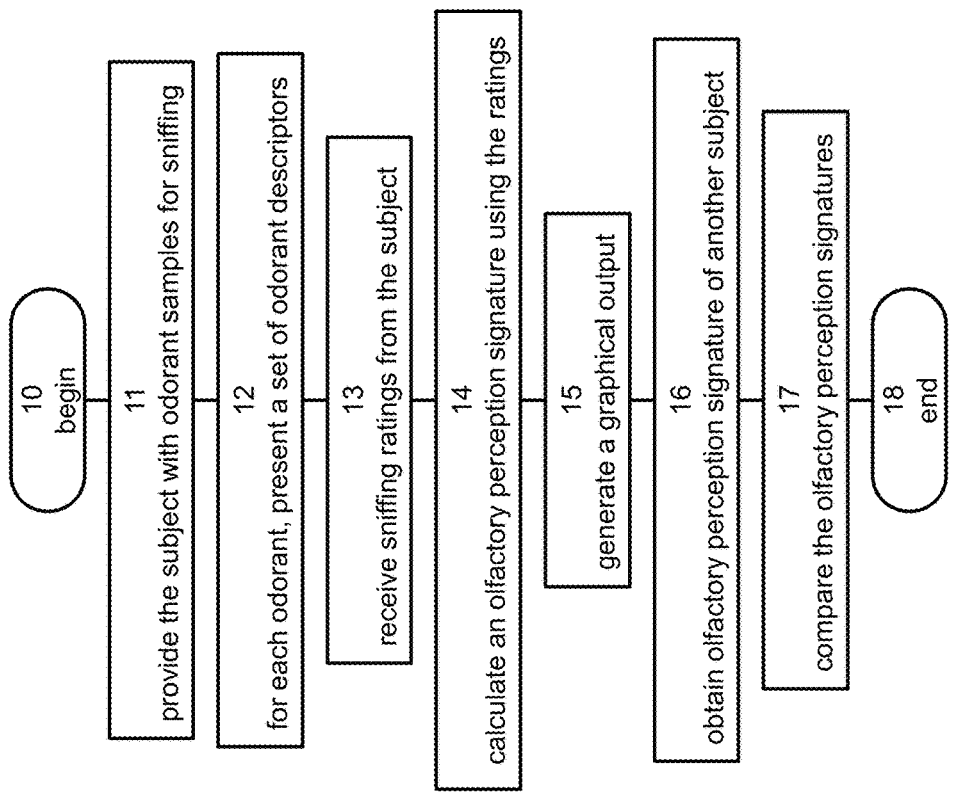

METHOD AND SYSTEM FOR DETERMINING OLFACTORY PERCEPTION SIGNATURE

FIELD AND BACKGROUND OF THE INVENTION

The present invention, in some embodiments thereof, relates to olfactory perception and, more particularly, but not exclusively, to a method and a system for determining olfactory perception signature.

Odors are complex mixtures of chemical species, and so contain many constituent molecules. The biological olfactory system is a remarkable sensor having many olfactory cells or odorant receptors, but not very many different types of olfactory cells. The characterization of a scent or odor is typically through the combined response of many of the receptors.

Because any two individuals differ by ~30% of their olfactory receptor subtype genome, this renders a potentially unique nose for each person. If one could capture this uniqueness with a perceptual test, a sort of perceptual olfactory fingerprint, this should then be informative on the underlying individual olfactory receptor subtype genome. The notion of a psychophysical test informing on underlying genes is of course well known from vision where color blindness charts inform about genes coding for different opsins in the retina.

U.S. Pat. No. 6,558,322 teaches methods and kits for determining olfactory perception. A test person's olfactory perception is evaluated and then determined by first providing the test subject with a palette of varying odors and fragrances, and then having that person describe, in full detail, each scent sample.

Background art includes Milinski M & Wedekind C (2001) *Behav Ecol* 12(2):140-149.

SUMMARY OF THE INVENTION

According to an aspect of some embodiments of the present invention there is provided a method of determining olfactory perception signature of a subject. The method comprises: providing the subject with a plurality of physical odorant samples for sniffing; for each sniffed odorant sample, presenting to the subject, by a user interface, a set of odorant descriptors and a respective set of rating controls, and receiving ratings entered by the subject using the rating controls. Each rating is indicative of a descriptiveness of a respective odorant descriptor for the odorant sample, thereby obtaining a set of descriptiveness levels for the odorant sample. The method also comprises calculating, by a computer, relations between pairs of sets of descriptiveness levels corresponding to pairs of odorant samples, to provide a vector of relations, wherein the vector represents the olfactory perception signature of the subject.

According to some embodiments of the invention the method comprises generating a graphical output describing the vector of relations.

According to some embodiments of the invention the method comprises obtaining an olfactory perception signature of another subject and comparing the olfactory perception signature of the subject with the olfactory perception signature of the other subject.

According to some embodiments of the invention the olfactory perception signature of another subject is obtained by accessing a computer readable database and selecting the olfactory perception signature of the other subject from the database.

According to some embodiments of the invention the method comprises, based on the comparison, determining likelihood for successful relationship between the subject and the other subject.

According to some embodiments of the invention the method comprises, based on the comparison, determining likelihood for Human leukocyte antigen (HLA) matching between the subject and the other subject.

According to some embodiments of the invention the comparison is by a metric selected from the group consisting of statistical correlation, Euclidian distance, Log-Euclidean distance, Angular distance, significance test distance, Chebyshev distance, Manhattan distance, and Minkowski distance.

According to some embodiments of the invention the method comprises: accessing a computer readable database, each entry of the database having a database olfactory perception signature and annotation information; searching the database for a database olfactory perception signature that is similar to the olfactory perception signature of the subject; and extracting from the database annotation information associated with the similar database olfactory perception signature.

According to some embodiments of the invention each annotation information of the database is a personality trait, and the method comprises determining a psychological condition of the subject based on the extracted annotation information.

According to some embodiments of the invention each of at least some annotation information of the database is selected from the group consisting of: openness to experience, conscientiousness, extraversion, agreeableness, and neuroticism.

According to some embodiments of the invention the method further comprises predicting an outcome of a psychological test for the subject, based on the extracted annotation information.

According to some embodiments of the invention the computer is remote from the user interface, and the method comprises transmitting the set of descriptiveness levels over a communication network to the computer.

According to an aspect of some embodiments of the present invention there is provided a method for matching members of an online community. The method comprises: providing to a member of the community a plurality of physical odorant samples for sniffing. At a client computer: receiving sniffing ratings entered by the member using rating controls of a user interface of the client computer, calculating an olfactory perception signature of the member based on the ratings, and transmitting the olfactory perception signature to a server computer. At the server computer: accessing a computer readable database having a plurality of database olfactory perception signatures of other members of the community searching the database for a database olfactory perception signature that is similar to the olfactory perception signature of the member, and transmitting to the client computer an indication that a similar database olfactory perception signature has been found.

According to some embodiments of the invention the method comprises displaying on the user interface a set of odorant descriptors for each odorant sample, wherein the sniffing ratings are indicative of descriptiveness of each odorant descriptor of the set.

According to some embodiments of the invention the calculation of the olfactory perception signature comprises calculating relations between pairs of sets of descriptiveness levels corresponding to pairs of odorant samples.

According to some embodiments of the invention the calculation of the relations comprises, for each pair of odorant samples, averaging squared differences between descriptiveness levels of a first odorant sample of the pair, and respective descriptiveness levels of a second odorant sample of the pair.

According to an aspect of some embodiments of the present invention there is provided a server system for communicating in a matching service for matching members of an online community. The server system comprises: a transceiver arranged to receive and transmit information on a communication network; and a processor arranged to communicate with the transceiver, and perform code instructions, comprises: code instructions for receiving from a client computer an olfactory perception signature of a member; code instructions for accessing a computer readable database having a plurality of database olfactory perception signatures of other members of the community; code instructions for searching the database for a database olfactory perception signature that is similar to the olfactory perception signature of the member; and code instructions for transmitting to the client computer an indication that a similar database olfactory perception signature has been found.

According to an aspect of some embodiments of the present invention there is provided a client system for communicating in a matching service for matching members of an online community. The client system comprises: a transceiver arranged to receive and transmit information on a communication network; and a processor arranged to communicate with the transceiver, and perform code instructions, comprises: code instructions for displaying a set of rating controls on a user interface; code instructions for receiving sniffing ratings entered by a member using the rating controls; code instructions for calculating an olfactory perception signature of the member based on the ratings; code instructions for transmitting the olfactory perception signature to a server computer; and code instructions for receiving from the server computer an indication whether or not a matching member has been found in a database, based on the transmitted olfactory perception signature.

According to some embodiments of the invention the processor is arranged to display on the user interface a set of odorant descriptors, respectively corresponding to the set of rating controls, wherein the sniffing ratings are descriptiveness levels corresponding to the odorant descriptors.

According to some embodiments of the invention the processor is arranged to display the set of odorant descriptors and the a set of rating controls a plurality of times, each times, and to receive the sniffing ratings a respective plurality of times, thereby to obtain a plurality of sets of descriptiveness levels, wherein the calculation of the olfactory perception signature comprises calculating relations between pairs of sets of descriptiveness levels.

According to some embodiments of the invention the calculation of the relations comprises, for each pair of sets, averaging squared differences between descriptiveness levels of a first set pair, and respective descriptiveness levels of a second set of the pair.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
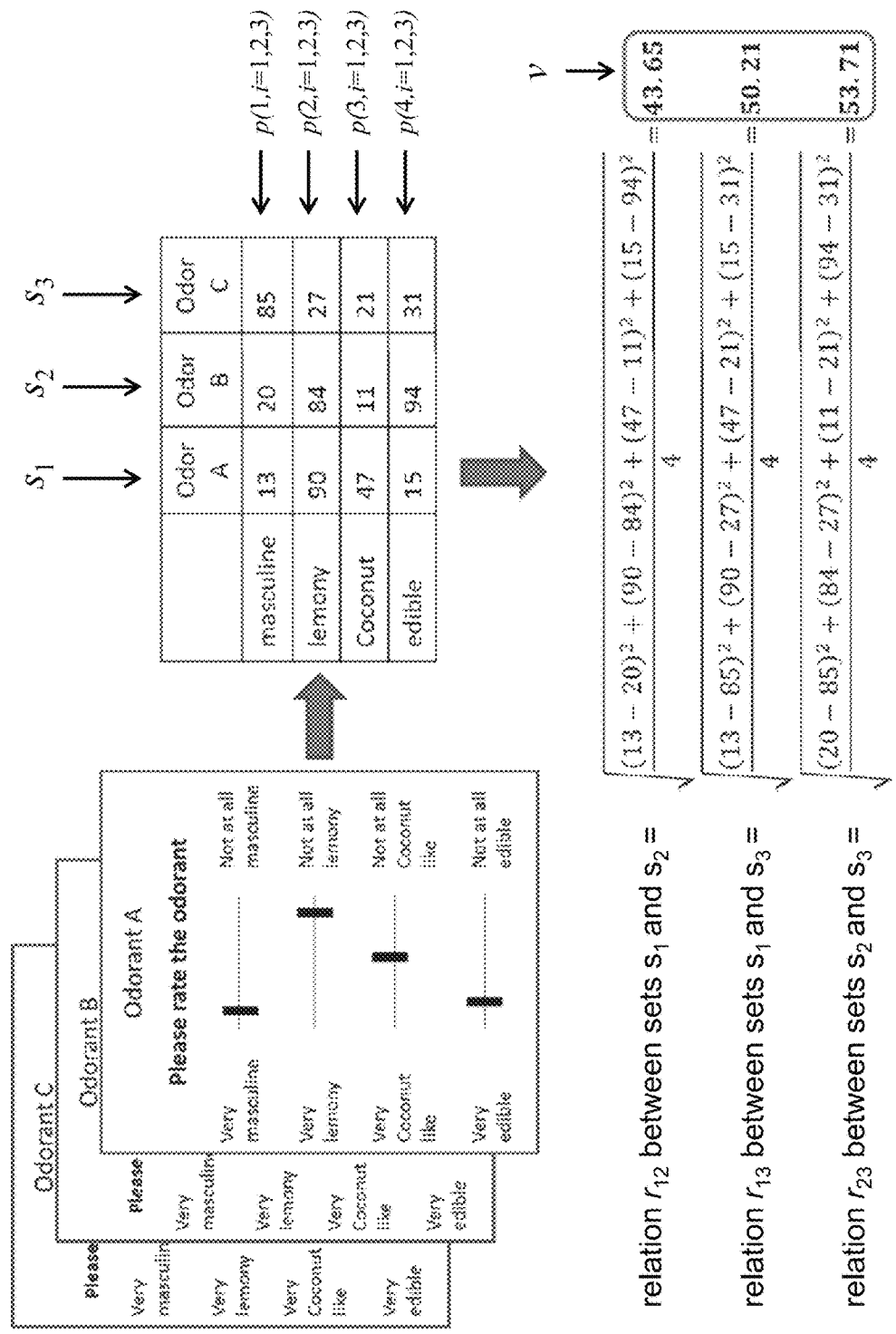

FIGS. 1A and 1B are schematic illustrations describing a technique for obtaining olfactory fingerprints, according to some embodiments of the present invention. Odorant ratings along visual-analogue scales (VAS) are converted into numbers reflecting location on the VAS line. Pairwise odorant relation is calculated as the distance across all descriptors used, and pairwise person similarity is calculated as the correlation across odors. All this assures that fingerprints are odorant-specific but descriptor-independent. For example, imagine John who was raised on an island smelling real coconuts, and Jane who knows coconut only from Bounty chocolate bars. "Coconut" is very different for these two individuals. John may rate Odor A as 47% like coconut, Odor B as 49% like coconut, and Odor C as 4% like coconut. Thus, odors A and B are highly similar, and both are dissimilar from odor C. Jane may rate same Odor A as 21% like coconut, Odor B as 19% like coconut, and Odor C as 100% like coconut. Once again, odors A and B are highly similar, and both are dissimilar from odor C. Thus, John and Jane will have very similar olfactory fingerprints derived from these three odorants and one descriptor, even though they are in total disagreement as to what coconut smell is like.

FIGS. 2A-G show olfactory fingerprints and their characterizations, according to some embodiments of the present invention. The fingerprints were consistent within individuals and different across individuals. To visualize fingerprints, 378 pairwise similarities were interpolated. A) An example olfactory fingerprint of one individual. B) The olfactory fingerprint of the same individual from A, but here derived using a different set of non-overlapping descriptors. C) The olfactory fingerprint of the same individual from A and B, but here obtained separately 16 days later. D) The olfactory fingerprint of a different individual. Correlations: A Û B, r=0.89; A Û C, r=0.61; A Û D, r=0.25. E) The best-correlated descriptors across all odors. F) Heat-map matrix of distances between all subject pairs. G) Histogram of correlation coefficients of all non self-self pairs.

Figure 3B:
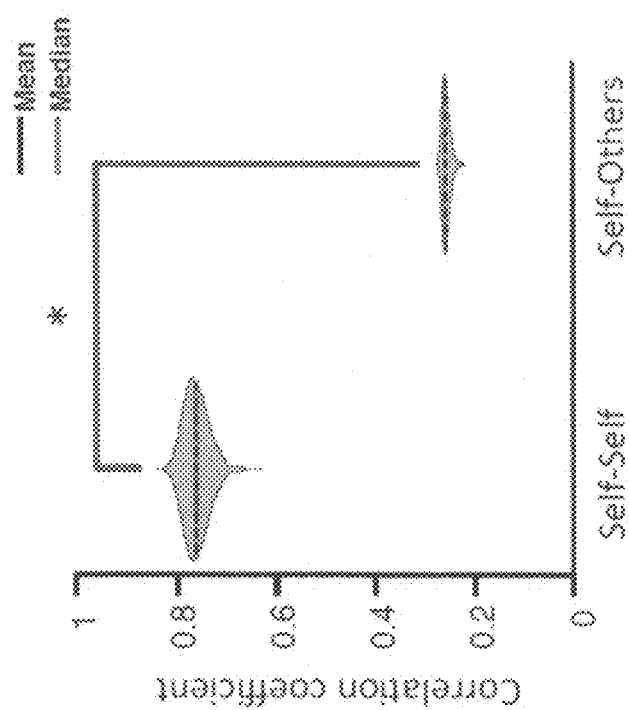
Figure 3A:
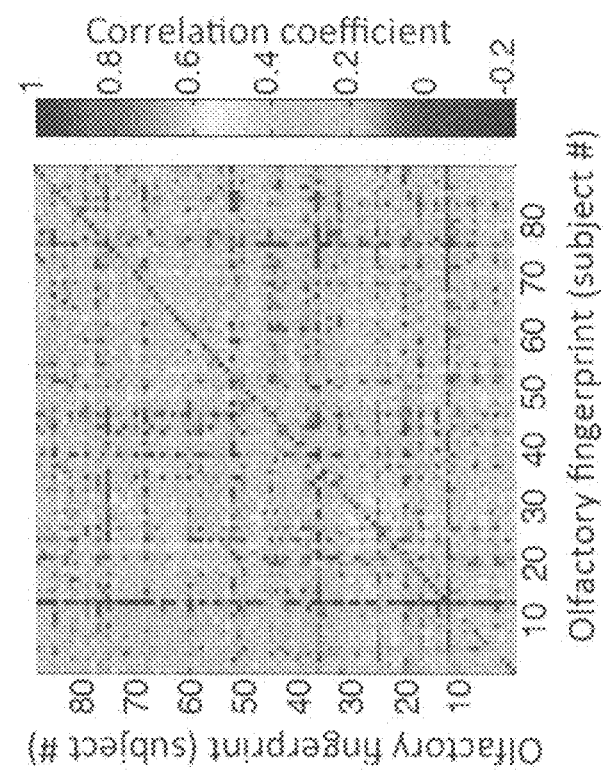

FIGS. 3A-B illustrate that olfactory fingerprints are independent of descriptor identity. A) Heat-map matrix of distances between fingerprints A and B for 89 subjects, where A and B were derived using the same odorants but different descriptors. The diagonal represents the correlation of a subject to him/herself. B) Violin plots comparing correlation coefficients of all self-self pairs (using different descriptors) to all self other pairs, the distribution of correlation coefficients of self-self and self-others are shown in orange, the mean and median of the distribution are depicted in black and red respectively.

FIGS. 4A-D illustrate that fingerprints depend on the number of odors and descriptors and the passing of time. A) Heat-map of fingerprint ability to distinguish self-self from self-other pairs (represented in Z-Score values) as a function of number of odors and descriptors used. Dashed line represents Z-Score value of 1.65 (p=0.05). B) 3D plot of Z-Score values as a function of number of odors and descriptors used to generate a fingerprint. C) First test-retest. Violin plot comparing correlation coefficients of 23 subjects refingerprinted across time. Left side represents correlation coefficients distribution of a subject to him/herself over time. Right side represents correlation coefficients distribution of a subject to other subjects over time. The mean and median of the distribution are depicted in black and red respectively. D) Second test-retest with five repetitions. Right Y axis is correlation across retests (r) shown in yellow. Left Y axis is the ability of the fingerprint to discriminate self from others in Z-score values when comparing the first to ensuing retests (black bars) or each two consecutive retests (red line).

Figure 5B:
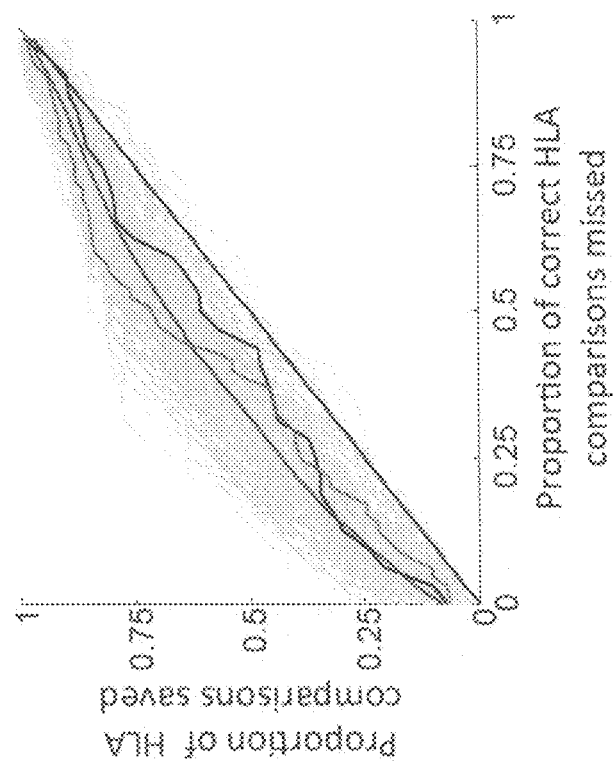
Figure 5A:
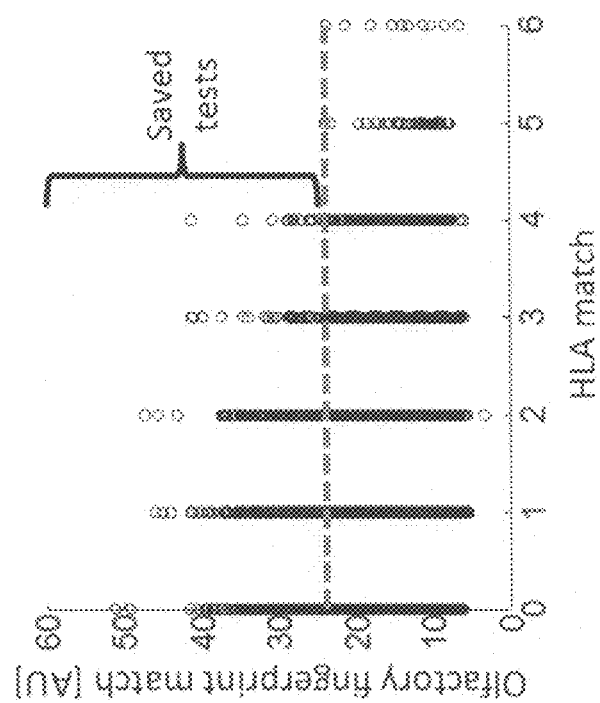

FIGS. 5A-B illustrate that similar olfactory fingerprints imply high Human leukocyte antigen (HLA) matching. A) 16770 pairwise comparisons of olfactory fingerprint distance vs HLA match. The dotted red line reflects the cutoff for saved tests. B) ROC curves of HLA comparisons saved vs. HLA matches missed. The diagonal identity line reflects no gain or loss. ROCs: Red=using all 11 odors, Gray=200 testing curves using 4 odorants, Black and Blue=median and mean of the 4 best odorants respectively.

FIGS. 6A-B are exemplary raw data showing the use of 54 descriptors in experiment 1A across all subjects and all odors. Some descriptors were rated zero for some odors; however, all of the descriptors were rated above 80 for some odors and subjects. (A) Dot plot. (B) Violin plot.

FIGS. 7A-B are exemplary raw data showing the use of 54 descriptors in experiment 2 across all subjects and all odors. Some descriptors were rated zero for some odors; however, all of the descriptors were rated above 80 for some odors and subjects. (A) Dot plot. (B) Violin plot.

FIGS. 8A-E. (A) An example of calculating the Z value for one subject. A Gaussian is fitted (magenta line) to the distribution of correlation coefficients (CC) between subject's fingerprint A of and all other subjects (blue bars). Z value of subject's CCs between fingerprint A and B (red bar) is calculated using the mean and SD obtained from the fitted Gaussian. (B) Distribution of olfactory fingerprint CC. (Upper) Distribution of CC between a subject and all other subjects. (Lower) Distribution of CC between a subject and him/herself. (C) PERMANOVA test to compare intrasubject distance to intersubject distance within the same session. Distribution of bootstrapped (flipped labels) PERMANOVA pseudo F values (blue bars) compared with the real pseudo F values (red arrow). (D) PERMANOVA test to compare intrasubject distance to intersubject distance between sessions. Distribution of bootstrapped (flipped labels) PERMANOVA pseudo F values (blue bars) compared with the real pseudo F values (red arrow). (E) Olfactory fingerprint distance vs. HLA match; 16,770 pairwise comparisons of olfactory fingerprint distance (calculated using CC) vs. HLA match value. Blue circles represent subject pairs with low (0-4) HLA match, green circles represent subject pairs with high (5, 6) HLA match.

FIGS. 9A-E. (A) An example of calculating the Z value for one subject. A Gaussian is fitted (magenta line) to the distribution of Euclidian distances (ED) between subject's fingerprint A of and all other subjects (blue bars). Z value of subject's ED between fingerprint A and B (red bar) is calculated using the mean and SD obtained from the fitted Gaussian. (B) Distribution of olfactory fingerprint ED. (Upper) Distribution of ED between a subject and all other subjects. (Lower) Distribution of ED between a subject and him/herself. (C) PERMANOVA test to compare intrasubject distance to intersubject distance within the same session. Distribution of bootstrapped (flipped labels) PERMANOVA pseudo F values (blue bars) compared with the real pseudo F values (red arrow). (D) PERMANOVA test to compare intrasubject distance to intersubject distance between sessions. Distribution of bootstrapped (flipped labels) PERMANOVA pseudo F values (blue bars) compared with the real pseudo F values (red arrow). (E) Olfactory fingerprint distance vs. HLA match; 16,770 pairwise comparisons of olfactory fingerprint distance (calculated using ED) vs. HLA match value. Blue circles represent subject pairs with low (0-4) HLA match, green circles represent subject pairs with high (5, 6) HLA match.

FIGS. 10A-E. (A) An example of calculating the Z value for one subject. A Gaussian is fitted (magenta line) to the distribution of log of Euclidian distances (LoED) between subject's fingerprint A and all other subjects (blue bars). Z value of subject's LoED between fingerprint A and B (red bar) is calculated using the mean and SD obtained from the fitted Gaussian. (B) Distribution of olfactory fingerprint LoED. (Upper) Distribution of LoED between a subject and all other subjects. (Lower) Distribution of LoED between a subject and him/herself. (C) PERMANOVA test to compare intrasubject distance to intersubject distance within the same session. Distribution of bootstrapped (flipped labels) PERMANOVA pseudo F values (blue bars) compared with the real pseudo F values (red arrow). (D) PERMANOVA test to compare intrasubject distance to intersubject distance between sessions. Distribution of bootstrapped (flipped labels) PERMANOVA pseudo F values (blue bars) compared with the real pseudo F values (red arrow). (E) Olfactory fingerprint distance vs. HLA match; 16,770 pairwise comparisons of olfactory fingerprint distance (calculated using LoED) vs. HLA match value. Blue circles represent subject pairs with low (0-4) HLA match, green circles represent subject pairs with high (5, 6) HLA match.

FIG. 11 is a flowchart diagram of a method suitable for determining olfactory perception signature of a subject, according to some embodiments of the present invention.

Figure 12:
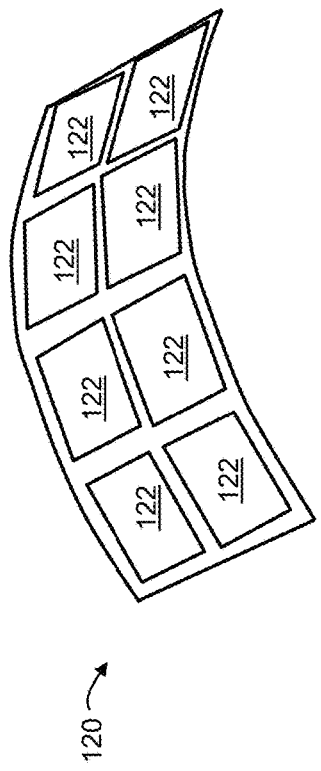

FIG. 12 is a schematic illustration of a collection of odorant samples, which can be used for determining olfactory perception signature according to some embodiments of the present invention.

Figure 13:
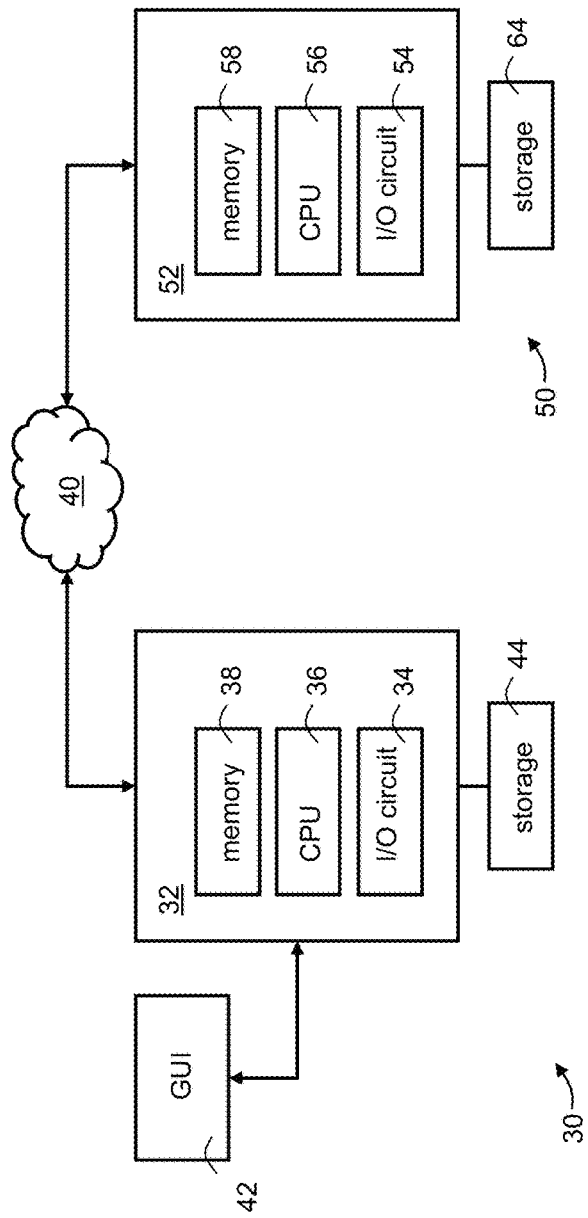

FIG. 13 is a schematic illustration of a client-server configuration which can be used for determining olfactory perception signature according to some embodiments of the present invention.

DESCRIPTION OF SPECIFIC EMBODIMENTS OF THE INVENTION

The present invention, in some embodiments thereof, relates to olfactory perception and, more particularly, but not exclusively, to a method and a system for determining olfactory perception signature.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 11 is a flowchart diagram of a method suitable for determining olfactory perception signature of a subject, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations described herein can be can be implemented by a data processing system, e.g., a dedicated circuitry or a general purpose computer, configured for receiving data and executing the operations described below. At least part of the operations can be implemented by a cloud-computing facility at a remote location. The data processing system or cloud-computing facility can serve, at least for part of the operations as an image processing system, wherein the data received by the data processing system or cloud-computing facility include image data.

Computer programs implementing the method of the present embodiments can commonly be distributed to users by a communication network or on a distribution medium such as, but not limited to, a floppy disk, a CD-ROM, a flash memory device and a portable hard drive. From the communication network or distribution medium, the computer programs can be copied to a hard disk or a similar intermediate storage medium. The computer programs can be run by loading the code instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Referring to FIG. 11 the method begins at 10 and optionally and preferably continues to 11 at which the subject is provided with a plurality of physical odorant samples for sniffing.

Each odorant sample can contain an odorant component or an odorant mixture containing a plurality of odorant components.

As used herein, an "odorant component" is a monomolecular substance which can be sensed by the olfactory receptors and is perceived as having a smell in humans.

Optionally and preferably, one or more of the odorant samples is in solid state, but odorant samples in liquid or gaseous states are also contemplated. In various exemplary embodiments of the invention at least 5 or at least 10 or at least 15 or at least 20 odorant samples are provided. Preferably the number of odorant samples is less than 50. The number of odorant samples is denoted below by M.

The M odorant samples can be provided in any form. For example, they can be provided as a scratch-and-sniff stickers or cards, liftoff-and-sniff stickers or cards, sniff-jars, sealed absorbing pads, and the like. A collection of odorant samples provided as scratch-and-sniff cards is illustrated in FIG. 12, showing an array 120 of eight scratch-and-sniff cards 122 each card containing an odorant component or an odorant mixture. It is appreciated that array 120 can include any number of cards 122, and that the subject can be provided with one, or more than one array 120.

Any odorant component or odorant mixture can be used for the odorant sample. A non-exhaustive list of possible odorant components or odorant mixtures includes, without limitation, root beer, cola, vanilla, chocolate, mint, peanut butter, apple, orange, grapefruit, peach, cinnamon, leather, ocean, burning rubber, cut grass, carrot, hard-boiled egg, butterscotch, strawberry, banana, blueberry, bubblegum, lavender, rose, pepper, clove, coffee, tea, tomato sauce, oregano, mustard, magic marker, pumpkin pie, raspberry, lemon, vinegar, dill, pineapple, sour apple, almond extract, licorice, cotton candy, popcorn, cherry, pine, chicken noodle soup, macaroni and cheese, hot dog, ginkgo, olive, apple pie, BBQ, birthday cake, candy corn, caramel, cheddar cheese, cherry pie, chili, fish, fresh bread, gingerbread, hamburger, pecan pie, hot dog, jelly bean, licorice, marshmallow, Mexican food, popcorn, pumpkin pie, roast beef, lemon lime, spaghetti, waffle, honey, root beer, spiced cider, apple, banana, blueberry, cherry, coconut, grape, green apple, lemon, lemonade, chocolate, chocolate mint, cola, cotton candy, peanut butter, pie crust, pina colada, almond, cucumber, dill pickle, carnation, daffodil, *gardenia*, general floral, geranium, hay, hibiscus, honey suckle, lawn, lilac, lily, *magnolia*, mulberry, orchid, pine, spruce pine, rose, wheat, tulip, sunflower, violet, hyacinth, maple, blue spruce, basil, butterscotch, black pepper, cinnamon, clove, garlic, hazelnut, mesquite, airy fresh, band-aid, balsam, baby powder, bergamot, bubble gum, cigar, frankincense, perfume, soothing, leather, menthol, money, new car, soap, sea breeze, suntan oil, tobacco, tooth paste, campfire, invigorating, uplifting, ash tray, compost, manure, jasmine, cedar, pine, juniper, ginger, myrrh, truffle, chocolate chip cookies, pizza, anchovy, anise, and *eucalyptus*.

In experiments performed by the present inventors the following odorant samples were used: moth ball, *eucalyptus*, strawberries, burnt rubber, sweat, natural gas, dill pickle, fish, cigar, manure, musk, ashtray, root beer, compost, green apple, cheese, mango, garlic, maple, anise, rose, blue spruce, clove, banana, banana (isoamyl acetate), *eucalyptus* (1,8-cineole), wet grass (cis-3-hexen-1-ol), and isovaleric acid.

Referring again to FIG. 11, at 12 the subject is presented with a set of odorant descriptors for each sniffed odorant sample. The odorant descriptors are optionally and preferably presented by a user interface such as, but not limited to, a graphical user interface displayed on a computer screen, a smart TV screen, or a screen of a mobile device, e.g., a smartphone device, a tablet device or a smartwatch device. In some embodiments, a set of rating controls is also displayed, preferably on the same screen.

The odorant descriptors are human-language descriptors and are presented in a human-readable form to allow the subject to read and decipher them. Typically, each of the descriptors is associated with a known odor, not necessarily odor that is emitted by one of the odorant samples, or a subjective perception of odor. For example, a descriptor can be a textual phrase, such as, but not limited to, "smells like coconut" or "smells like rubber" or "does not smell like gasoline" or "has a pleasant smell" or "has an unpleasant smell" or the like.

The number of odorant descriptors is not necessarily the same as the number of odorant samples. It was found by the present inventors that a relatively small number of odorant descriptors is sufficient for determining the olfactory perception signature of the subject. The number of odorant descriptors can therefore be smaller than the number of odorant samples. For example, the number of odorant descriptors can be from about 5 to about 15. The number of odorant descriptors is denoted below by N.

While embodiments in which N<M are preferred, it is to be understood that embodiments in which N=M or N>M are also contemplated.

The rating controls that are displayed can be of any type generally known in the field of graphical user interface design. Representative examples include, without limitation, a slider, a dropdown menu, a combo box, a text box and the like. A representative set of human-language descriptors with a respective set of rating controls is illustrated in FIG. 1A.

Odorant descriptors sets that are presented at 12 for different odorant samples need not to be disjoint sets. In preferred embodiments, an intersection set of at least two sets of odorant descriptors (one set for each odorant sample) is a non-empty set, so that there is at least one or at least two or more odorant descriptors (which are elements of the intersection between the sets) that is/are presented at 12 for two different odorant samples. In some embodiments, the same set of odorant descriptors is repeatedly presented for all odorant samples.

At 13, sniffing ratings are received from the subject. In embodiments in which rating controls are displayed, the user enters the ratings in the rating controls, and the ratings are received from the rating controls. Each received rating is indicative of a descriptiveness of the respective odorant descriptor for the respective odorant sample, as perceived by the subject upon sniffing that odorant sample. For example, when the odorant descriptor is "has a pleasant smell," the sniffing rating indicates to what extent the subject perceives the pleasantness of the odor of the respective odorant.

Since the subject is presented with a set of N odorant descriptors for each odorant sample, the method preferably obtains at 13 a set s of perceived descriptiveness levels $p(1,k), p(2,k), \ldots, p(N,k)$ for each odorant sample k. The descriptiveness levels are preferably numerical according to a predetermined scale, for example, 0 to 100. The ratings, on the other hand, are not necessarily numerical. For example, the ratings can be positions on a slider or textual phrases from a dropdown menu. In embodiments in which the ratings are not numerical, the method optionally and preferably parses the ratings and maps them to numerical descriptiveness levels according to a predetermined mapping protocol. It is appreciated, however, that some subjects may not provide a rating for each and every odorant descriptor that is displayed, since, for example, some subjects may find a particular odorant descriptor irrelevant for a particular odorant sample. In such a scenario, the method can exclude the particular descriptiveness level from the set of descriptiveness level that corresponds to the respective odorant sample, so that the size of the set s is less than N for the respective odorant sample. Alternatively, the method can substitute a value for that particular descriptiveness level, according to a predetermined procedure, so that the size of the set s remains N. The substituted value is preferably a statistical measure, such as, but not limited to, the mean or median of all descriptiveness levels that were obtained from the subject for the same odorant descriptor after sniffing other odorant samples.

Once all the ratings are received for all the odorant samples, a collection C, including M sets $s_1, s_2, \ldots, s_M$ of descriptiveness levels, is obtained.

At 14, an olfactory perception signature of the subject is calculated based on the ratings. This is optionally and preferably executed by calculating relations between pairs of sets of the collection C, which pairs of sets correspond to pairs of odorant samples. This provides a vector v of relations, which vector represents the olfactory perception signature of the subject. The dimension of the vector v is therefore equal to or less than $M(M-1)/2$ which is the numbers of pairs in the collection C. Thus, denoting the relation between set $s_i$ of collection C and set $s_j$ of collection C by $r_{ij}$, where $i,j \leq M(M-1)/2$, the components of the vector v are $r_{12}, r_{13}, r_{23}$, etc. When the vector v has its maximal dimension $M(M-1)/2$, namely when all possible pairwise relations are calculated, the vector v can be written as $v=(r_{12}, r_{13}, \ldots, r_{1M}, r_{23}, \ldots, r_{M-1,M})$.

The relations can be calculated in more than one way. In one embodiment, squared differences $(p(k,i)-p(k,j))^2$ between descriptiveness levels $p(k,i)$ of a first odorant sample i of the pair, and respective descriptiveness levels $p(k,j)$ of a second odorant sample j of the pair are calculated. The squared differences can be averaged for each pair (i,j) of odorant samples, for example, by summing over the odorant descriptor index k, and dividing by the size N of the sets s. Thereafter, a square root of this average is optionally and preferably obtained to provide the relation value $r_{ij}$ between odorant sample i and odorant sample j (or, equivalently between set $s_i$ and set $s_j$). These embodiments are schematically illustrated in FIG. 1A.

It is appreciated that such a calculation of the relation $r_{ij}$ is equivalent to a normalized Euclidian distance between two vectors $u_i=(p(1,i), p(2,i), \ldots, p(N,i))$ and $u_j=(p(1,j), p(2,j), \ldots, p(N,j))$ each vector being formed of one set of descriptiveness levels and therefore represent one odorant sample, wherein the normalization factor is the square root of the dimension of the vectors $u_i$ and $u_j$ (the number of descriptiveness levels in each set).

In another embodiment, the relation $r_{ij}$ is calculated using a non-Euclidian distance between the two vectors $u_i$ and $u_j$. Optionally, the non-Euclidian distance can be normalized by the square root of the dimension of the vectors. Representative examples of non-Euclidian distance include, without limitation, a Chebyshev distance, a Manhattan distance, and a Minkowski distance. Other relations between pairs of sets, such as a statistical correlation (e.g., Pearson correlation, Spearman correlation, Kendall correlation) or a t-test distance between the vectors $u_i$ and $u_j$, are also contemplated.

In cases in which a relation $r_{ij}$ is calculated for vectors of different size the calculation optionally and preferably includes only descriptiveness levels that correspond to odorant descriptors to which the subject provided ratings for both odorant samples i and j.

The relations $r_{ij}$ provide indication regarding the similarity between the respective sets. It is appreciated that whether the calculated relation $r_{ij}$ increases or decreases with the level of similarity between the sets depends on the procedure employed for calculating the relations $r_{ij}$. For example, when the calculation is based on distances (Euclidian distance, non-Euclidian distance, t-test distance), high value of the calculated relations $r_{ij}$ indicates low similarity level, and when the calculation is based on correlation, high value of the calculated relations $r_{ij}$ indicates high similarity level.

The method can optionally and preferably proceed to 15 at which a graphical output describing the vector of similarities is generated. The graphical output can be a color coded output. A representative example of such an output is shown in FIGS. 2A-E, described in greater detail in the Examples section that follows.

The method can optionally and preferably proceed to 16 at which an olfactory perception signature of another subject is obtained and to 17 at which the olfactory perception signatures are compared. The comparison can be based, for example, on a metric selected from the group consisting of statistical correlation (e.g., Pearson correlation, Spearman correlation, Kendall correlation), Euclidian distance, Log-Euclidean distance, Angular distance, significance test (e.g., t-test) distance, Chebyshev distance, Manhattan distance, Minkowski distance and the like. Thus, for example, a distance or statistical correlation between the olfactory perception signatures can be calculated and the calculated value of the distance or statistical correlation can be used as a similarity measure describing the level of similarity between the two signatures. For example, when a statistical correlation is calculated, higher correlation value indicates higher similarity between the signatures, and when an Euclidian distance, a Log-Euclidean distance, a non-Euclidean distance, an Angular distance or a significance test distance is calculated, lower distance value indicates higher similarity between the signatures.

The comparison can be utilized in more than one way. In some embodiments, the comparison is utilized for matching between members of a community, e.g., an online community. For example, based on the comparison, a likelihood for successful relationship between the subject and the other subject can be determined, wherein when the signatures are more similar the likelihood for successful relationship is higher and when the signatures are less similar the likelihood for successful relationship is lower.

In some embodiments, the comparison is utilized for determining likelihood for HLA matching between the subject and other subject, wherein when the signatures are more similar the likelihood for HLA matching is higher and when the signatures are less similar the likelihood for HLA matching is lower. As demonstrated in the Examples section that follows, it was found by the present Inventors that similarity between the olfactory fingerprints of the present embodiments is significantly higher for highly HLA-matched individuals than for poorly HLA-matched individuals.

The olfactory perception signature of the other subject can be calculated as described above. Alternatively, the olfactory perception signature to which the subject's signature is compared can be obtained from an entry in a database of olfactory perception signatures.

Each entry in such a database can include olfactory perception signature and annotation information. The annotation information can be stored separately from the olfactory perception signature (e.g., in a separate file on a computer readable medium). The annotation information corresponds to the individual or individuals for which the database olfactory perception signature pertains. For example, the annotation information can include details of the community member that is characterized by the database olfactory perception signature. The annotation information can alternatively or additionally include HLA data of the individual that is characterized by the database olfactory perception signature.

Also contemplated are embodiments in which the annotation information relates to psychological traits, for example, each olfactory perception signature can be associated with a psychological trait (e.g., openness to experience, conscientiousness, extraversion, agreeableness, neuroticism), and a high similarity between the signature of the subject and the database signature can be indicative that the subject can be described by the respective psychological trait. Thus, a search within a database of psychologically annotated olfactory perception signatures allows determining the psychological condition of the subject, and/or predicting an outcome of a psychological test for the subject.

Representative examples of psychological tests for which the results can be predicted by the present embodiments include, without limitation, NEO-PI, 16PF, Occupational Personality Questionnaire, Beck Depression Inventory, Glover Numbing Scale, Eysenck Personality Questionnaire, Life Experiences Survey, Perceived Stress Scale, State-Trait Anxiety Inventory (STAI) Form Y-2, STAI Form Y-1, Pittsburgh Sleep Quality Index, Kohn Reactivity Scale, Pennebaker Inventory for Limbic Languidness, Short Form 12 Health Survey v2, SF-36, Pain Catastrophizing Scale, In vivo Coping Questionnaire, Coping Strategies Questionnaire-Rev, Lifetime Stressor List& Post-Traumatic Stress Disorder (PTSTD) Checklist for Civilians, Multidimensional Pain Inventory v3, Comprehensive Pain & Symptom Questionnaire, Symptom Checklist-90-R (SCL-90R), Brief Symptom Inventory (BSI), Beck Depression Inventory (BDI)1 Profile of Mood States Bi-polar, Pain Intensity Measures, and Pain Unpleasantness Measures.

The method ends at 18.

The determination of olfactory perception signature and the optional comparison to another olfactory perception signature can be executed according to some embodiments of the present invention by a server-client configuration, as will now be explained with reference to FIG. 13.

FIG. 13 illustrates a client computer 30 having a hardware processor 32, which typically comprises an input/output (I/O) circuit 34, a hardware central processing unit (CPU) 36 (e.g., a hardware microprocessor), and a hardware memory 38 which typically includes both volatile memory and non-volatile memory. CPU 36 is in communication with I/O circuit 34 and memory 38. Client computer 30 preferably comprises a graphical user interface (GUI) 42 in communication with processor 32. I/O circuit 34 preferably communicates information in appropriately structured form to and from GUI 42. Also shown is a server computer 50 which can similarly include a hardware processor 52, an I/O circuit 54, a hardware CPU 56, a hardware memory 58. I/O circuits 34 and 54 of client 30 and server 50 computers preferable operate as transceivers that communicate information with each other via a wired or wireless communication. For example, client 30 and server 50 computers can communicate via a network 40, such as a local area network (LAN), a wide area network (WAN) or the Internet. Server computer 50 can be in some embodiments be a part of a cloud computing resource of a cloud computing facility in communication with client computer 30 over the network 40.

GUI 42 and processor 32 can be integrated together within the same housing or they can be separate units communicating with each other. GUI 42 can optionally and preferably be part of a system including a dedicated CPU and I/O circuits (not shown) to allow GUI 42 to communicate with processor 32. Processor 32 issues to GUI 42 graphical and textual output generated by CPU 36. Processor 32 also receives from GUI 42 signals pertaining to control commands generated by GUI 42 in response to user input. GUI 42 can be of any type known in the art, such as, but not limited to, a keyboard and a display, a touch screen, and the like. In preferred embodiments, GUI 42 is a GUI of a mobile device such as a smartphone, a tablet, a smartwatch and the like. When GUI 42 is a GUI of a mobile device, processor 32, the CPU circuit of the mobile device can serve as processor 32 and can execute the code instructions described herein.

Client 30 and server 50 computers can further comprise one or more computer-readable storage media 44, 64, respectively. Media 44 and 64 are preferably non-transitory storage media storing computer code instructions as further detailed herein, and processors 32 and 52 execute these code instructions. The code instructions can be run by loading the respective code instructions into the respective execution memories 38 and 58 of the respective processors 32 and 52. Storage media 64 preferably also store one or more databases including a database of psychologically annotated olfactory perception signatures as further detailed hereinabove.

In operation, processor 32 of client computer 30 displays on GUI 42 a set of rating controls, such as, but not limited to, a slider, a dropdown menu, a combo box, a text box and the like. Preferably, processor 32 also displays on GUI 42 a set of odorant descriptors, respectively corresponding to the set of rating controls, as further detailed hereinabove and exemplified in the upper left pane of FIG. 1A. A subject, which can be a member of an online community, and which is provided with physical odorant samples (e.g., samples 122) for sniffing, enters the sniffing ratings using the rating controls displayed on GUI 42.

Processor 32 receives the subject's ratings from GUI 42 and can calculate an olfactory perception signature of the subject based on these ratings. For example, similarities between pairs of sets of descriptiveness levels can be calculated to provide a vector of similarities as further detailed hereinabove. Processor 32 can then transmit the olfactory perception signature to server computer 50.

Alternatively, processor 32 can receive the subject's ratings from GUI 42 and transmit these ratings to server computer 50. In these embodiments, the calculation of the olfactory perception signature of the subject, based on the transmitted ratings, is executed by server computer 50, e.g., by calculating the similarities between pairs of sets to provide a vector of similarities as further detailed hereinabove.

Server computer 50 can access a database of olfactory perception signatures stored on media 64, search searches the database for a database olfactory perception signature that is similar to the olfactory perception signature of the subject, and, when such similar database signature is found, transmit to client computer 30 an indication that a similar database olfactory perception signature has been found. Client computer 30 can receive the indication from server computer 50 and display it on GUI 42.

Server computer 50 can also transmit to client computer 30 the annotation information associated with the similar database signature, and client computer 30 can display this information on GUI 42. For example, when the comparison between signatures is for the purpose of social matching, the server computer 50 can pull from the database member details pertaining to the member associated with the found database signature, and transmit these details to client computer 30 for displaying on GUI 42.

As used herein the term "about" refers to ±10%.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral)

within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL METHODS

Subjects

A total of 238 generally healthy subjects participated in three experiments.

Experiment 1A: 89 subjects, 40 women, mean age=$25.7\pm3.1$ years; Experiment 1B: 18 subjects, 11 women, mean age $26.8\pm3.4$; Experiment 2: 130 subjects, 65 women, mean age=$29.93\pm8.44$ years).

Odorants

Two forms of odorant presentation were used in this study. Experiment 1A contained 24 odorants in scratch-and-sniff form provided by The PrintBox Inc (NY, USA) and 4 odorants presented in sniff-jars. Experiment 1B contained 22 odorants presented in sniff-jars. Experiment 2 contained 11 odorants all in jars; the 4 jar odorants from Experiment 1 (isoamyl-acetate, 1,8-cineole, cis-3-hexen-1-ol, isovaleric acid) and 7 additional odorants. Because the initial test-retest experiment used mostly scratch-and-sniff odorants and the second test-retest experiment used jars, any difference between these methods of presentation could be assessed. No significant difference in test-retest was found when comparing scratch-and-sniff (r=$0.59\pm0.14$) to jars (r first-second=$0.58$, $\pm0.21$, $t(39)=0.24$, $p=0.81$).

List of Odorants Used for Experiment 1A

1. Moth ball; 2 *Eucalyptus;* 3 Strawberries; 4 Burnt rubber; 5 Sweat; 6 Natural gas; 7 Dill pickle; 8 Fish; 9 Cigar; 10 Manure; 11 Musk; 12 Ashtray; 13 Root beer; 14 Compost; 15 Green apple; 16 Cheese; 17 Mango; 18 Garlic; 19 Maple; 20 Anise; 21 Rose; 22 Blue spruce; 23 Clove; 24 Banana; 25 Banana (isoamyl acetate); 26 *Eucalyptus* (1,8-cineole); 27 Wet grass (cis-3-hexen-1-ol); 28 Isovaleric acid.

Odorants 1-24 were presented as scratch-and-sniff cards (obtained from The Print Box, Inc.). Odorants 25-28 were single molecules presented in small jars.

List of Descriptors Used for Experiment 1A

1. Fishy; 2 Sour milk; 3 Hot cool; 4 Coconut; 5 Aromatic; 6 Fresh eggs; 7 Crushed grass; 8 Anise; 9 Burnt candle; 10 Household gas; 11 Almond; 12 Fruity (not citrus); 13 Citrus; 14 Creosote; 15 Cologne; 16 Floral; 17 Chocolate; 18 Oily/fatty; 19 Medicinal; 20 Woody/resinous; 21 Pleasant; 22 Nutty; 23 Nail polish remover; 24 Strawberry; 25 Poisonous edible; 26 Mild/intense; 27 Annoying/soothing; 28 Pleasant; 29 Familiar; 30 Weak/strong; 31 Sweet; 32 Clean/dirty; 33 Causes physical tension/causes physical relaxation; 34 Feminine; 35 Fresh/stale; 36 Dull/sharp; 37 Volatile; 38 Repulsive/attractive; 39 Nose stuffing/nose opening; 40 Artificial/natural; 41 Burnt; 42 Erotic; 43 Green; 44 Medicinal; 45 Salty; 46 Hot/cold; 47 Bitter; 48 Sour; 49 Heavy/light; 50 Smoked; 51 Poisonous/edible; 52 Masculine; 53 Disgusting.

List of Odorants Used for Experiment 1B

1. Ambrarome absolu; 2 Anisic aldehyde/aubepine; 3 Castoreum artess resin 246/2 IFR; 4 Carvone laevo; 5 *Cistus labdanium* oil Spain RB; 6 Civet artessence absolute; 7 *Eucaliptus globulus* oil China; 8 Fennel oil sweet; 9 Fir balsam oil Canada; 10 *Galbanum* oil concentrated; 11 Ginger ol; 12 Grapefruit oil California; 13 Guava duplcation CS; 14 Hexanol 3-CIS; 15 Hydrocarboresin SB; 16 Jasmin absolute communelle; 17 Nutmeg oil Indonesia; 18 Pepper black oil; 19 Peppermint oil; 20 Peru balsam oil; 21 Vitiver oil Haiti; 22 Mugest C5 RIFM.

List of Descriptors Used for Experiment 1B

1. Body odor; 2 Pleasant; 3 Fresh/rotten; 4 Sweet; 5. Poisonous/edible; 6 smooth/textured; 7 Flowery; 8 Feminine; 9 Light/heavy; 10 Erotic; 11 Cold/hot; 12 Weak/strong; 13 Burnt; 14 Sour; 15 Masculine; 16 Complex; 17 Clean/dirty; 18 Artificial/natural; 19 Calming/disturbing; 20 Dull/sharp; 21 Bitter; 22 Dry/wet; 23 Aromatic.

Ratings

Each subject rated 28 odorants along 54 verbal descriptors in Experiment 1A, 22 odorants along 23 verbal descriptors in Experiment 1B, and 11 odorants along 57 verbal descriptors in Experiment 2, using visual analogue scales (VAS). For example, the question "please rate the odorant" was displayed together with a 14 cm line ranging from "not at all smells like coconut" at one end, to "very much smells like coconut" at the other end. After sniffing the odorant presented in scratch-and-sniff or jar, participants crossed the line at a point reflecting their perception, and the line was later parsed to 100 for analysis. Odor order was random across participants, and inter-odor-interval was >40 seconds. To account for individual differences in use of scales, each subject's data was normalized by first subtracting the minimal value applied by the subject, then dividing by the maximal remaining value, and multiplying by 100. This generated a normalized range between 0 and 100.

HLA Typing 5-10 mL of blood were drawn from each volunteer and kept at 4° C. until DNA was extracted. Genomic DNA Extraction was carried out from 400 µL of whole blood using the MagNA Pure Compact Nucleic Acid Isolation Kit I (Roche Diagnostics GmbH, Mannheim, Germany). DNA samples were stored at −20° C. HLA typing was performed utilizing LUMINEX™ technology and Immucor Transplant Diagnostic (Stamford, Conn.) kits to obtain HLA A*, B* and DRB1* loci typings at low/intermediate resolution.

HLA Matching

HLA match was calculated using methods previously reported in reference (16). There are three general groups of HLA: HLA-A*, HLA-B* and HLADRB1*, and within each group there are different specific HLA proteins (there are 59 different HLA-A* proteins, 118 different HLA-B* and 124 different HLA-DRB1*). Each of these HLA groups (A*, B* and DRB1*) is notated by a 2-digit numerical designation (e.g. HLA-A* 01:07 HLA-B* 15:15, HLA-DRB1* 15:33). A match is calculated by counting the number of HLA proteins (in each group separately) present in one subject that are also present in another subject. Since there are 2 digits for each HLA group, the count can be 0, 1 or 2. Once the count for each HLA group is obtained, a match is calculated by summing the values of all the groups. In other words, for each donor/recipient pair, the number of antigens present in the donor that matched an antigen in the recipient were counted. Homozygous antigens in the recipient that matched a donor antigen were counted as two matches. Since three HLA loci were counted, there was a potential for a maximum of 7 matches. For example if donor A has the following HLA genotype A*24,68 B*14,35 DRB1* 01, 11 and recipient B has the following HLA genotype A*03,23 B*41, 47 DRB1*10,11 this pair (A→B) will have an HLA match score of 0+0+1=1. However if donor C has the following HLA genotype A*02, 30 B* 13, 50 DRB1* 07, 07 and recipient D has the following HLA genotype A*02, 02 B*27, 41 DRB1*07, 11 then the pair (C→D) will have an HLA match score of 2+0+1=3 and the pair (D→C) will have an HLA match score of 1+0+2=3 (note that even though the total HLA match score is the same it is not symmetric between C<→D).

Distance Metrics

The present embodiments contemplate several types of metrics to calculate the distance between olfactory fingerprints. In the present Example, three different distance metrics were used to define the distance between olfactory fingerprints of subject i and subject j (i.e. $d_{i,j}$). These include, (A) Correlation, (B) Euclidean distance, and (C) Log-Euclidean distance. These metrics were compared, and their impact on discriminability and stability were evaluated. In all metrics, the olfactory fingerprint FP was calculated in the same manner (see EQs. 1 and 2 below). The notation $FP_i^A$ denotes fingerprint of subject i, generated using set A of descriptors or during session A and $FP_j^B$ denotes fingerprint of subject j, generated using set B of descriptors or during session B. To evaluate the effectiveness of each method several indices were defined.

a) Z-value index: Comparison of within-subject (intrasubject) distance to between-subjects (intersubject) distance by using different descriptors during the same session. This index can be determined for each subject by calculating how many SDs his/hers intersubject's score lies from the mean of the distribution of intrasubject scores (the distribution of intrasubject scores is calculated only between one subject and all others).

To calculate the Z-Value, a Gaussian was fitted to the distribution of all intrasubject distances and calculated the mean and standard deviation of the fitted Gaussian. Then the quantity $$Z_j = \left(\frac{x_j - \mathrm{mean}(x_i)}{sd(x_i)}\right) i \neq j$$

was calculated for determining how far from the mean an individual typically falls. Thus, for each row of the distances matrix, the value in the diagonal of the matrix was compared to a Gaussian fitted to the distribution of all non-diagonal values. The individual Z-scores were averaged and to obtain an average Z-value index.

b) PERMANOVA Pseudo-F value: Permutational Multivariate ANOVA (PERMANOVA) was used to compare intrasubject distance to intersubject distance. PERMANOVA implements a flexible non-parametric distance-based analogue of analysis of variance for multivariate data that provides a distribution-free means of testing differences between treatments in their multivariate profile (Anderson, 2001).

c) Same as (a) but using same descriptors during the different sessions.

d) Same as (b) but using same descriptors during the different sessions.

e) P-value index: Using Wilcoxon rank sum test to compare olfactory fingerprint distance of low and high HLA match.

1. Distance Metric A: Correlation

Figure 8A:
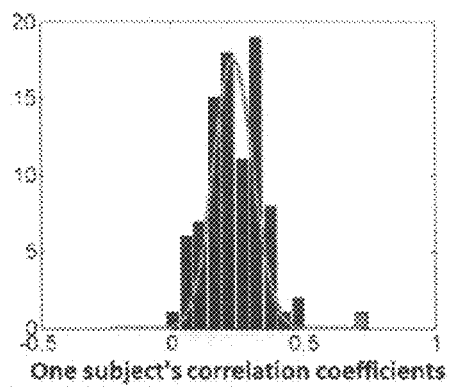
Figure 8B:
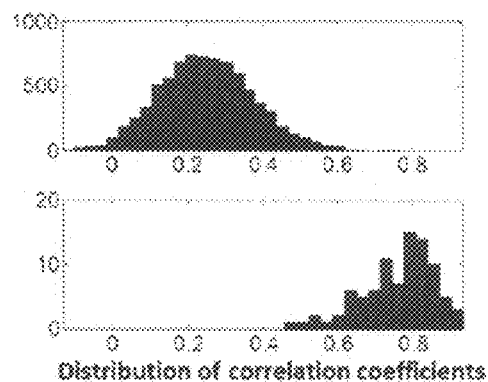
Figure 8C:
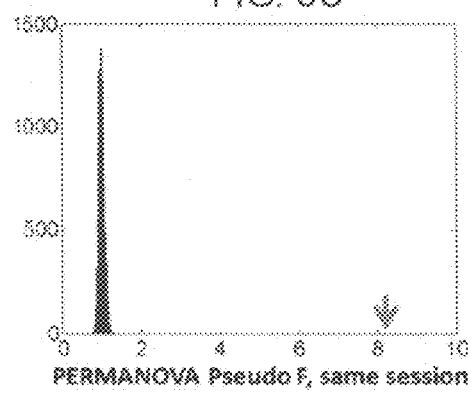
Figure 8D:
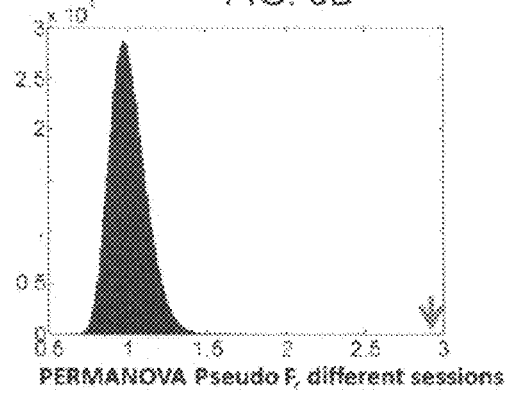
Figure 8E:
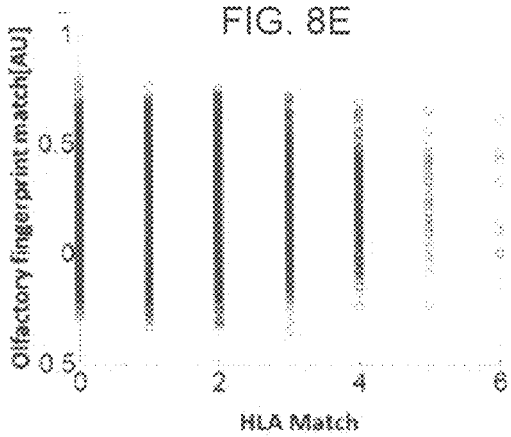

Pearson correlation was used as a metric for distances ($d_{i,j}$) between olfactory fingerprints, $d_{i,j}$=corrolation($FP_i^A$, $FP_j^B$), more specifically, $d_{i,j}$=COV($FP_i^A$,$FP_j^B$)/($\sigma(FP_i^A)\sigma(FP_j^B)$), where COV denotes a covariance as and $\sigma$ denotes a standard deviation of the respective olfactory fingerprint.

a. Different descriptors comparison, see (a) above: Mean difference between individual's two fingerprints d=0.76±0.02, mean difference between two different individual's fingerprints d=0.25±0.007. Average Z-value Z=4.91. FIGS. 8A-B.

b. PERMANOVA test comparing intrasubject distance to intersubject distance within the same session but using different descriptors: pseudo F=8.16, $p<10^{-6}$. FIG. 8C.

c. Different sessions comparison, see (b) above: Mean difference between an individual's two fingerprints: d=0.58±0.15, mean difference between two different individual's fingerprints d=0.31±0.076, Average Z-value Z=2.67.

d. PERMANOVA test comparing intrasubject distance to intersubject distance between two sessions: pseudo F=4.23, $p<10^{-6}$. FIG. 8D.

e. Wilcoxon rank sum test comparing olfactory fingerprint distance of low and high HLA match: Z=2.14, p<0.03. FIG. 8E.

2. Distance Metric B: Euclidean Distance

We used Euclidean distance as a metric for distances ($d_{i,j}$) between olfactory fingerprints:

$$d_{i,j}=\sqrt{\Sigma_{i=1}^{n}(FP_i^A-FP_j^B)^2} \quad \text{Formula:}$$

Figure 9A:
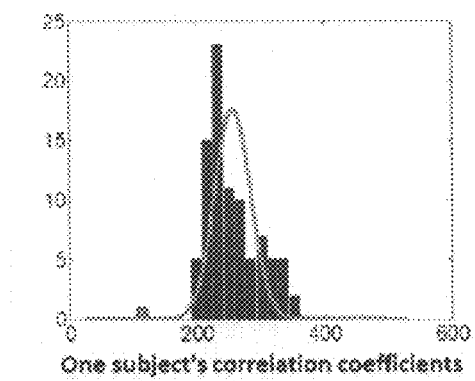
Figure 9B:
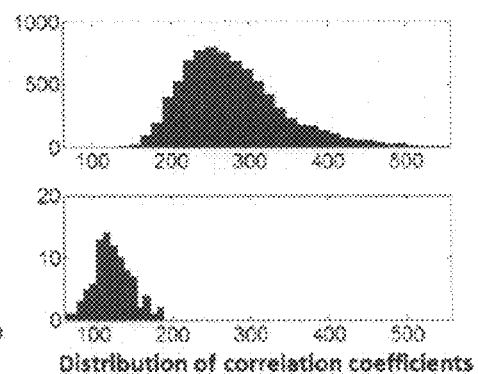
Figure 9C:
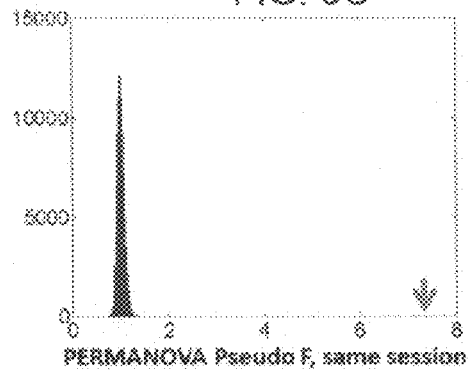
Figure 9D:
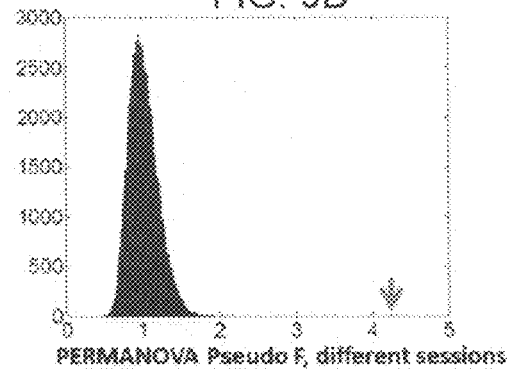
Figure 9E:
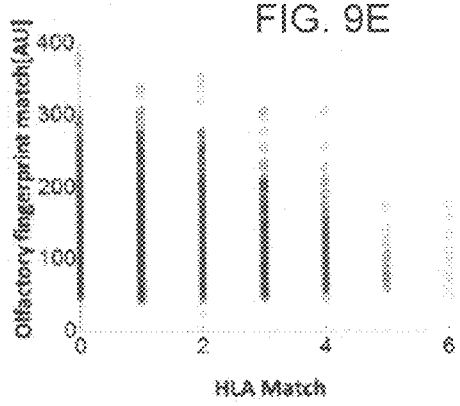

Note: when using Euclidean distance as a metric for distances, the distribution of olfactory fingerprints distances (d) is not Gaussian; hence a Z-score value might not be a good candidate for comparison intrasubject to intersubject distance.

a. Different descriptors comparison, see (a) above: Mean difference between an individual's two fingerprints d=140±29, mean difference between two different individual's fingerprints d=280±34. Average Z-value Z=2.82. FIGS. 9A-B.

b. PERMANOVA test to compare intrasubject distance to intersubject distance within the same session but using different descriptors: pseudo F=7.3, $p<10^{-6}$. FIG. 9C.

c. Different sessions comparison, see (b) above: Mean difference between an individual's two fingerprints: d=200±42, mean difference between two different individual's fingerprints d=320±41, Average Z-value Z=1.75.

d. PERMANOVA test to compare intrasubject distance to intersubject distance between two sessions: pseudo F=4.23, $p<10^{-6}$. FIG. 9D.

e. Wilcoxon rank sum test comparing olfactory fingerprint distance of low and high HLA match: Z=3.21, p<0.0015. FIG. 9E.

3. Distance Metric C: Log-Euclidean Distance

Figure 10A:
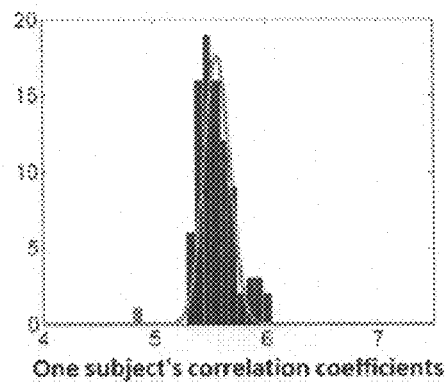
Figure 10B:
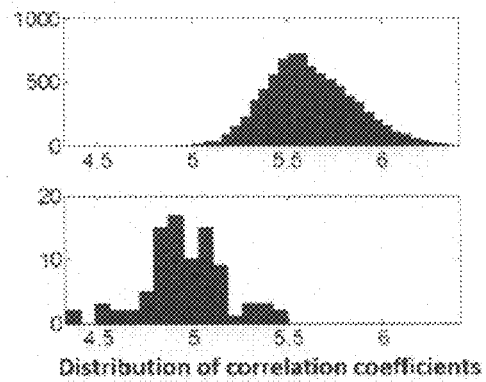
Figure 10C:
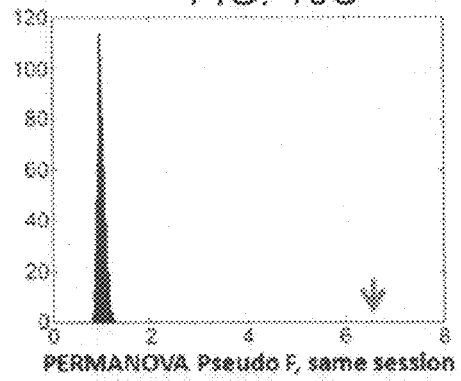
Figure 10D:
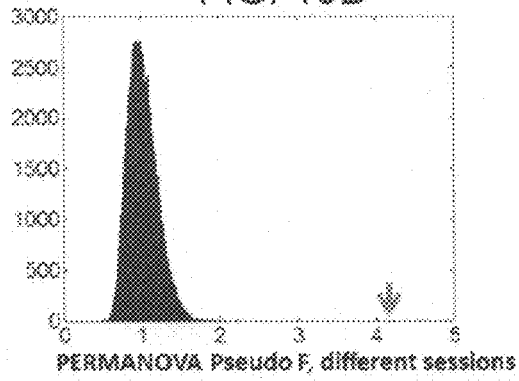
Figure 10E:
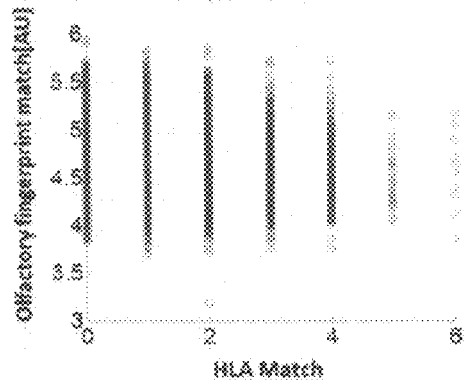

To reshape the distribution of Euclidean distances (see 2 above) be more Gaussian log of Euclidean distance was used as a metric for distances ($d_{i,j}$) between olfactory fingerprints:

$$d_{i,j}=\log(\sqrt{\Sigma_{i=1}^{n}(FP_i^A-FP_j^B)^2}) \quad \text{Formula:}$$

a. Different descriptors comparison, see (a) above: Mean difference between an individual's two fingerprints d=5±0.22, mean difference between two different individual's fingerprints d=5.6±0.1. Average Z-value Z=3.47. FIGS. 10A-B.

b. PERMANOVA test to compare intrasubject distance to intersubject distance within the same session but using different descriptors: pseudo F=6.5, $p<10^{-6}$. FIG. 10C.

c. Different sessions comparison, see (b) above: Mean difference between an individual's two fingerprints: d=5.3±0.2, mean difference between two different individual's fingerprints d=5.7±0.13, Average Z-value Z=2.23.

d. PERMANOVA test to compare intrasubject distance to intersubject distance between two sessions: pseudo F=4.23, $p<10^{-6}$. FIG. 10D.

e. Wilcoxon rank sum test comparing olfactory fingerprint distance of low and high HLA match: Z=3.21, p<0.0015. FIG. 10E.

Derivation of Olfactory Fingerprints

Fingerprints were derived using a matrix of perceived odor similarities (21). A palette of 28 odors (listed above) that provided for 378 pairwise similarities (28×27/2=378). Such a 378-dimensional olfactory fingerprint allows for characterization of many individuals.

Rather than directly obtaining pairwise relation estimates, the present inventors derived pairwise relation from 54 different descriptors applied to each odorant alone (listed above). A derived relation rating, as opposed to a direct relation rating, was selected because whereas the two are highly correlated, derived relation is much easier and faster to obtain. For example, direct relation ratings of the 378 possible odorant pairs in this study would entail 756 individual odorant presentations (A vs. B×378) each followed by one question: "rate similarity". Such a large number of odorant presentations (756) may be difficult to process by a human subject. On the other hand, 378 derived relation ratings entail 28 odorant presentations each followed by several questions (e.g., "rate how coconut", "rate how lemony", etc), and derivation of relation from the answers. This remains a feasible experiment, and moreover, the number of questions can later be reduced based on the current analysis.

Use of odorant descriptors likely entails personal (23) and cultural differences (24), yet the technique optionally and preferably does not assume or rely on any agreement across individuals in the application of a given descriptor (FIGS. 1A and 1B contain a schematic of fingerprint acquisition that explains this issue). Thus, an individual olfactory fingerprint was calculated by computing all the pairwise distances between all odorants rated. For a measure of distance between odorant k and odorant m, the following equation was used:

$$distance_{k,m} = \sqrt{\frac{\sum_{i=1}^{n}(P_i^k - P_i^m)^2}{n}} \quad \text{(EQ. 1)}$$

Where $P_i^k$ is the perceptual rating of odorant k using descriptor i. and $P_i^m$ is the perceptual rating of odorant m using descriptor i. In words: the distance between odorant k and odorant m is the square root of the mean of the squared difference between all perceptual ratings for those two odorants. Once all the pairwise distances are computed, an olfactory fingerprint may be notated in the following form:

$$FP_{k+m-1} = \text{distance}. \quad \text{(EQ. 2)}$$

Where k=1 . . . N and m=k+1 . . . N. In words; each element of the olfactory fingerprint is the distance between pairs of odorants, where each pairwise distance is calculate only once (since $distance_{k,m} = distance_{m,k}$) and the distance between an odorant to itself is omitted (since $distance_{k,k} = 0$). Consequently, if N odors are uses to construct an olfactory fingerprint the resulting olfactory fingerprint will have N×(N−1)/2 elements. To negate the impact of variance in the number of descriptors used by subjects (e.g., one subject may have used only 50 of the 54 descriptors, and another only 45, leaving all other descriptors unrated, see FIGS. 6A-B and 7A-B for descriptor usage), each distance between odor-pairs was normalized by the number of mutual descriptors used for this pair. For example, if odors A and B were rated along 50 descriptors by subject 1 and 45 descriptors by subject 2, the distance between odor pairs was dividing by √50 for subject 1 and by √45 for subject 2, thereby allowing direct comparison of the perceived distances between odors A and B for subject 1 and 2.

The derivations of relation according to some embodiments of the present invention do not assume that people agree with each other along any given descriptor (e.g., "how coconut"), they only assume that a person agrees with him/herself (FIGS. 1A and 1B). In other words, such relation matrices are odor dependent, but descriptor-independent. This was verified in experiments where fingerprints for the same individual obtained with the same odorants but different descriptors remained highly correlated.

For fingerprint visualization purposes, a rectangular image was generated by interpolating the 378 fingerprint values to 500 values. Then, these values were projected onto a 25×20 matrix, and a two-dimensional interpolation was conducted, providing a 2K×2K matrix, which were then projected onto a semi-circle (FIGS. 2A-D). This visualization technique was applied for 89 subjects (40 women, mean age=25.7±3.1 years).

Olfactory Fingerprints were Individually Specific

To test whether olfactory perception is similar across individuals, the present inventors calculated the mean rating along each descriptor for each odorant, and then calculated the correlation of each individual with the mean. Note, here fingerprints are not being compared, but rather ratings along specific descriptors. This revealed that individuals are indeed similar to each other in their gross perception. For example, in all top 10 correlated descriptors the mean perception was a very good predictor of individual perception (all r>0.68) (FIG. 2E). Moreover, the primary perceptual dimension of odor pleasantness (2, 26) was particularly highly correlated across individuals and odors, at r=0.73±0.1 (FIG. 2E). In other words, the average description of an odorant using common descriptors is a pretty good estimation of what any given individual will say about that odor.

Figure 2F:
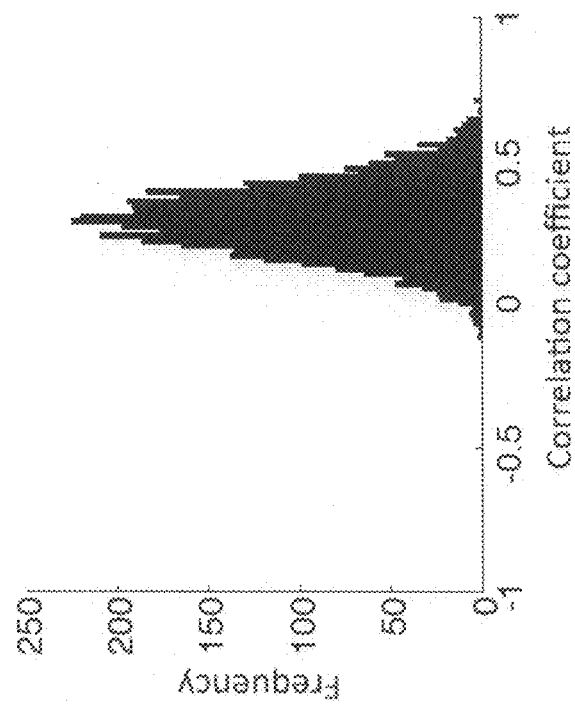
Figure 2G:
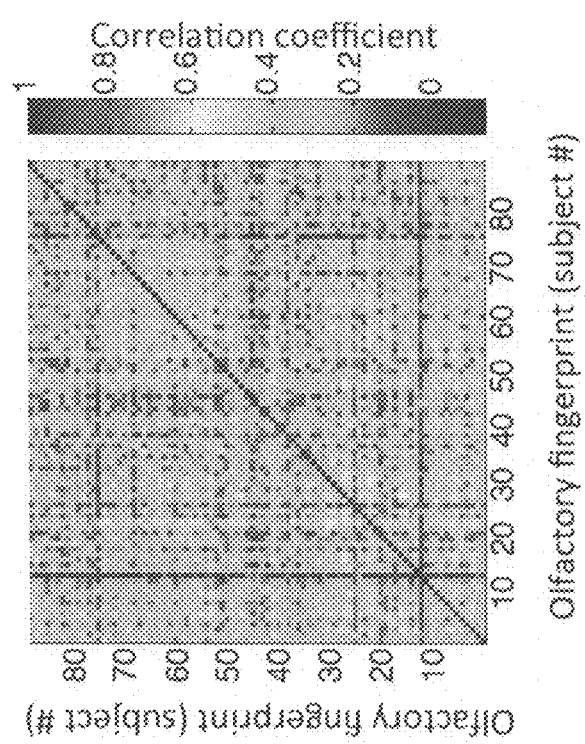

The present inventors next set out to determine whether despite this gross agreement on odor perception, the sensitive perceptual test of the present embodiments can uncover a unique olfactory perceptual fingerprint. Consistent with this hypothesis, it was found that across the 89 subjects that were tested, no two subjects had the same fingerprint (e.g., FIG. 2A vs. FIG. 2D, FIG. 2F and FIG. 2G). The present inventors calculated all pairwise distances between olfactory fingerprints (using Pearson's correlation) and found that the average correlation across individuals (omitting self-self) was r=0.3±0.13 (FIG. 2G). In other words, whereas gross perception was similar across individuals, a fine measure of perception revealed individual perception for each of the 89 subjects that were tested.

Olfactory Fingerprints were Independent of Descriptor Identity

The emergence of 89 individual fingerprints alone does not necessarily imply that individual olfactory perception was captured because one can obtain such a result (89 different fingerprints) with random odor relation ratings. To verify that olfactory fingerprints captured individual olfactory perception, for each of the 89 Participants, the present inventors now generated two alternative fingerprints, A and B, each utilizing a random independent half of the descriptors used to derive relation. They computed a matrix of all the pairwise distances between olfactory fingerprints A and B (89×89) and tested whether the distance of a subject from him/herself (using different descriptors) was smaller than the distance of a subject to anyone else. In other words whether, despite the use of different descriptors each time, a subject remained more similar to him/herself than to anyone else (distance between fingerprints was estimated by correlation, see General methods, herein above). This was repeated 1000 times, each time selecting a different set of nonoverlapping descriptors for fingerprints A and B, and the distances between fingerprints was assessed.

The present inventors again plotted the heat-map correlation matrix of each individual with all other individuals, this time however each pairwise distance is computed as the correlation between olfactory fingerprints A and B (FIG. 3A). It was found that the distance between an individual's two fingerprints based on the same odors but different descriptors (the diagonal in FIG. 3A, and FIG. 2A vs. FIG. 2B) was overwhelmingly smaller than the average distance between two different individuals (non-diagonal values in FIG. 3A and FIG. 2A vs. FIG. 2D) (mean difference between an individual's two fingerprints r=0.75±0.025, mean difference between two different individual's fingerprints r=0.25±0.008, paired t-test, t (999)=885.7, p<10$^{-10}$) (FIG. 3B). It was also found that the maximum of the heat-map correlation matrix lies on the diagonal (i.e. self-self correlation). In other words, olfactory fingerprints A and B of the same individual were always more similar than olfactory fingerprints of different individuals. The analysis of this data was repeated using a Permutational Multivariate ANOVA (PERMANOVA) to compare the distance between an individual's two fingerprints based on the same odors but different descriptors (e.g., FIG. 2A vs. FIG. 2B) to the distance between two different individuals (e.g., FIG. 2A vs. FIG. 2D). PERMANOVA implements a flexible non-parametric distance-based analogue of analysis of variance for multivariate data that provides a distribution-free means of testing differences between treatments in their multivariate profile (27). Again, the mean difference between an individual's two fingerprints was r=0.75±0.025, while the mean difference between two different individual's fingerprint was r=0.25±0.008 (PERMNOV test, pseudo F=8.16, p<$10^{-6}$) (FIG. 8C). Thus, the fingerprint genuinely captured personal identity, and a subject's odorant-specific olfactory fingerprint remains unique even when different descriptors are used to construct it. Once the present inventors established the main effect using PERMANOVA, they set out to extrapolate the ability of the olfactory fingerprint to identify an individual beyond their sample. For this one needs to calculate whether a subject's correlation to him/herself (calculated between fingerprints A and B) is within the distribution of correlations of a subject to all other subjects (between fingerprint A of a subject to fingerprint A of all other subjects). In other words: in order to conclude that a subject has a unique fingerprint the intersubject correlation should not belong (low probability) to the distribution of intrasubject correlations. They fitted a Gaussian to the intrasubject distances distribution, then calculated how many SDs a intersubject's score lies from the mean of the distribution of intrasubject scores (i.e Z-Value). From this they determined the probability of a subject's correlations to him/herself to be within the distribution of correlations of a subject to all other subjects (i.e. p-value). All the individual Z-Value scores were averaged, and the overall p-value was calculated. The distribution of correlations of a subject to all other subjects is not Gaussian, and the subject's correlation to him/herself is limited by 1 (or −1) hence other metrics for distance between subjects may yield modestly different results (see General Materials and methods). They repeated this procedure 1000 times, each time randomly halving the descriptors used to derive relation (with one half used to generate fingerprint A and the other half used to generate fingerprint B), and averaged across all iterations, and all subjects. They obtained an average Z-Value of 4.9 that corresponds to an ability to use the 28-odor olfactory fingerprint to identify one person out of about two million individuals.

Fingerprint Specificity

Figure 4A:
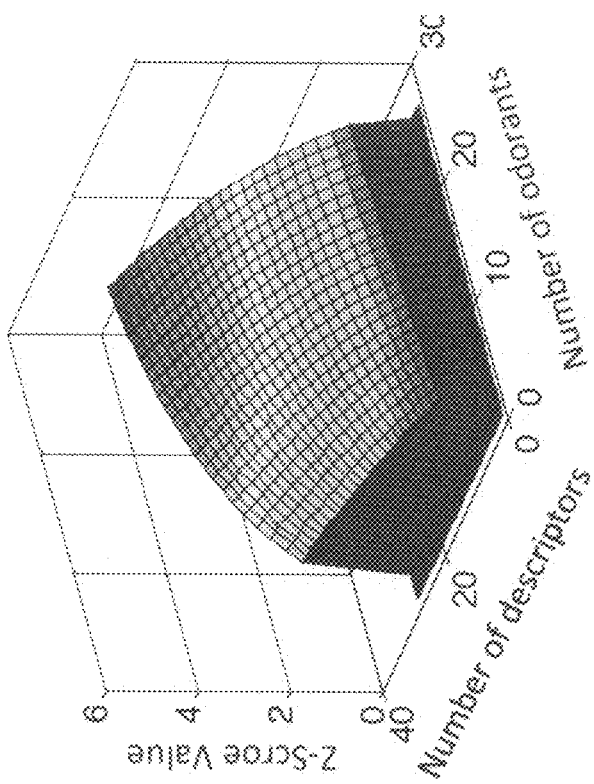
Figure 4B:
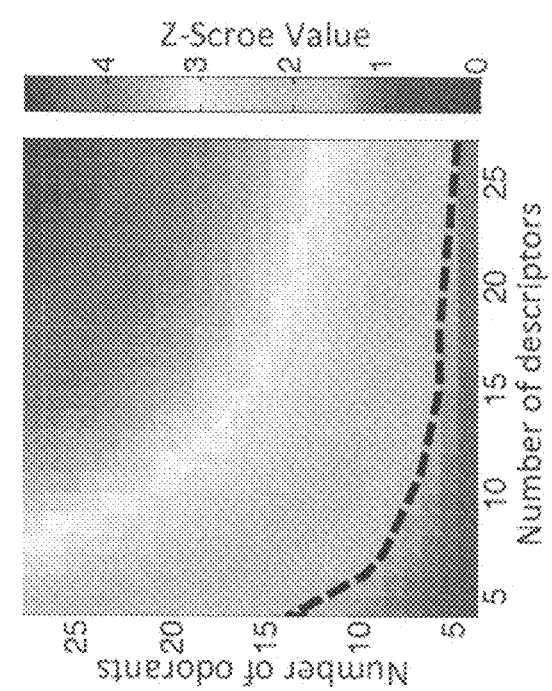

In initial experiments, as many as 54 descriptors and 28 odors were used because the present inventors wanted to explore the impact of these parameters. To estimate the dependence of fingerprint discriminability on the number of descriptors and odorants used, the present inventors again generated two alternative fingerprints for each subject, A and B, each utilizing a random independent half of the descriptors used to derive relation. Here, however, the number of odorants and descriptors used was successively reduced. Each analysis was repeated 1000 times, each time shuffling the particular odorants and descriptors omitted. The averaged fingerprint specificity (averaging the Z-Score across subjects and iterations) was plotted as a function of the number of descriptors and odorants used to generate it (FIGS. 4A, 4B). A monotonic decrease in the specificity of the fingerprint was observed, yet even with only 7 odors and 11 descriptors the correlation between an individual's two fingerprints based on the same odors but different descriptors was significantly above the correlation between two different individuals z=1.65, p<0.05. Thus, meaningful olfactory fingerprints can be obtained in under 10 minutes. In turn, the present inventors extrapolated to estimate how many odors and descriptors were necessary in order to obtain an individual fingerprint for each of the ~7 billion people on earth, and reached at 34 odors and 35 descriptors. Obtaining such a detailed fingerprint would take approximately 5 hours.

Olfactory Fingerprints Remained Specific Despite Fluctuation Over Time

Figure 4D:
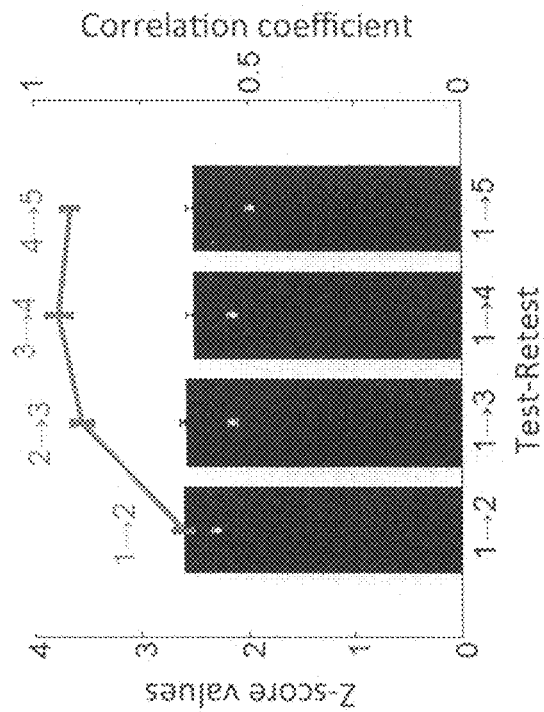
Figure 4C:
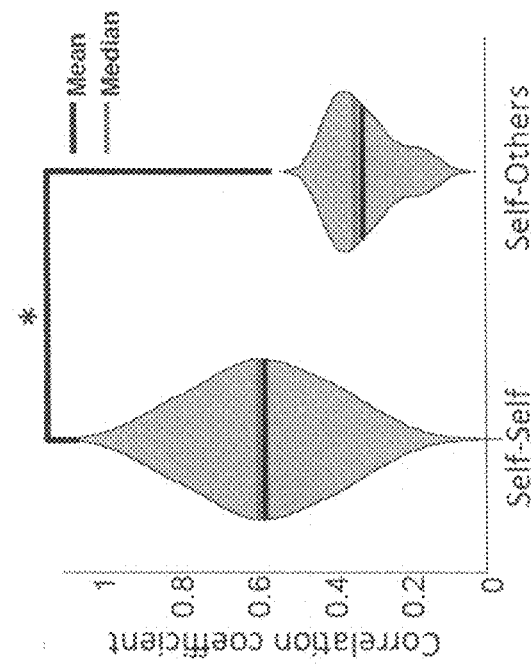

Olfactory perception is not only variable across individuals; it is also highly variable within individuals over time (28). This variability may reflect in part that odor perception is the combination of a given receptor activation pattern with the fluctuating homeostatic state in which it is perceived (hunger/satiety, mood, arousal, etc.) (2). To test the persistence of the olfactory fingerprint at retest, 23 participants were refingerprinted at a time ranging between 10 and 30 days following their initial fingerprinting (e.g., FIG. 2A vs. FIG. 2C). It was found that the average distance of a person from him/herself remained significantly lower than the average distance between different individuals (mean difference between an individual's two fingerprints over time r=0.58±0.15, mean difference between two different individual's fingerprints r=0.31±0.076, paired t test, t (44)=7.69, p<10−8) (FIG. 4C). In other words, despite the passage of time, a person remained significantly more correlated with him/her self than with others.

Despite the above result, the slight reduction in self-self correlation over retests raises the concern that given additional retests the self-self correlation advantage may disappear altogether. To address this concern the present inventors refingerprinted an additional group of 18 subjects across five fingerprinting sessions that spanned 14 to 30 days (list of odorants and descriptors for experiment 1B provided in the materials and method section). A repeated measures ANOVA revealed that at each repetition (II, III, IV, V) the average distance of a person from his/her first fingerprint remained unchanged (F(17,3)=2.24, p=0.09, mean difference between an individual's two fingerprints across retests r first-second=0.58±0.21, r first-third=0.54±0.18, r first-fourth=0.54±0.2, r first-fifth=0.49±0.19) (FIG. 4D yellow). Moreover, the fingerprint stability in fact improved after the first retest (F(17,3)=6.08, p<0.001) such that the second to third (r=0.66±0.19), third to fourth (r=0.68±0.20), and fourth to fifth (r=0.69±0.16) repetitions were all significantly better than the first to second (r=0.58±0.21, all t(17)>2.67, all p<0.02) (FIG. 4D). Taken together it may be concluded that despite the passage of time and repeated testing, a person remained significantly more correlated with him/her self than with others. The present inventors recalculated the ability of the olfactory fingerprint to identify an individual beyond the sample, this time comparing the initial and the later (few weeks later) fingerprints with the all the other subjects, and observed a decreased yet significant discriminability (z1-2=2.67, p<0.01, z1-3=2.67, p<0.01, z1-4=2.67, p<0.01, z1-5=2.67, p<0.01) (FIG. 4D black and red). This amounts to an ability to use the current olfactory fingerprint to identify one subject out of about three hundred individuals. Moreover, given this variability over time, to effectively obtain long-lasting olfactory fingerprints for the entire world population it was found by extrapolation that rather than 34 odors with 35 descriptors 160 odors are needed with 35 descriptors. Note that this reduced discriminability is not only because of the extent of shift in fingerprint over time; selfcorrelation over time decreased from r=0.75 to r=0.58, which remains significantly higher than the correlation across individuals. However, because on average all subjects shifted in this way, the ability to identify one person out of a crowd is significantly reduced.

Similar Olfactory Fingerprints Imply High HLA Matching

The hypothesis underlying the present effort was that fingerprints would provide a unique perceptual counterpart of an individual's unique olfactory receptor subtype genome. Consistent with this notion, 28-odor based fingerprints were special to the tune of 1-in-two million. The present inventors set out to test whether olfactory fingerprints can nevertheless remain informative of genetic traits linked to olfaction, in this case HLA. To test this the present inventors studied an additional 130 subjects (65 women, mean age=29.93±8.44 years) who provided blood samples for HLA typing (see methods), and olfactory fingerprints using the following 11 odors:
1. Isoamyl acetate
2 Vanillin
3 Isovaleric acid
4 cis-3-hexen-1-ol, wet grass
5 Androstadienone
6 Dibutyl amine
7 Ethyl pyrazine: 2-ethyl pyrazine
8 Eucalyptol (1,8-cineole)
9 Hexanol: 1-hexanol
10 Methyl anthranilate
11 Tolualdehyde: Ortho-tolualdehyde Combinatorically, 130 subjects provide for 16770 possible donor-recipient pairs. This is because HLA match is not symmetric, i.e., in a given pair, a subject can have a high HLA match as a donor but poor HLA match as a recipient (note that the terms donor and recipient are used to describe the directionality of HLA matching). Therefore, 130 subjects resulted in 16770 possible pairs (130*129) and not in 8385 (130*129/2). For each pair, an olfactory fingerprint match was calculated using Euclidean distance (see materials and methods) and an HLA match along a seven point scale (0-6, 0=no match) previously described (16). Only 65 out of 16770 possible pairs of individuals had a high HLA match of 5 or 6 (FIG. 5A).

It was found that the olfactory fingerprint match of these individuals was significantly better than the olfactory fingerprint match for poorly HLA-matched individuals (HLA 5-6: mean olfactory fingerprint match in arbitrary units (AU) of Euclidean distance=12.7±4.1 [A.U.], HLA 1-4: mean olfactory fingerprint match=14.6±5.3 [A.U.], Wilcoxon rank sum test: Z=3.2, p<0.0015). In other words, the olfactory perceptual fingerprint similarity was significantly informative on HLA matching, implying that it captured meaningful genetic information.

To further assess the strength of the link between olfactory fingerprint match and HLA match, the present inventors asked what would happen if one used olfactory fingerprints to screen for potentially high HLA matches in the population. To this end, the percentage of high HLA matches one would potentially miss (incurred cost) versus the percentage of matches one could identify (gain) was calculated and presented using a receiver operating characteristic (ROC) curve (red line—FIG. 5B).

It was found that all points in the ROC curve fall above the identity-line; hence the olfactory fingerprints of the present embodiments can identify pairs of individuals likely to have a high HLA match. Given the extended time needed to test 11 odorants as carried out in data collection, the present inventors next asked if they could optimize this test.

To this end, the data were halved into training (8387 subject pairs) and testing sets (8385 subject pairs), each maintaining the original fractions of each level of HLA match. In the training set, the olfactory fingerprints was calculated using all possible combinations of 3 to 11 odorants, and the 4 best-performing odorants were selected and then tested in the testing set. This was repeated 200 times (gray lines—FIG. 5B). Taking the median score (black line—FIG. 5B), it was found that a selection of 4 odors (Isoamyl acetate, Isovaleric acid, 2-Ethyl Pyrazine, and 1-Hexanol) decreased the average olfactory fingerprint distances of high HLA matched individuals to 10.8±3.7 [A.U.] compared to an olfactory fingerprint distance for poorly HLA matched individuals of 13.8±5.8 [A.U.] (Z=4.35, p<0.000015).

The actual savings implicated were calculated as follows. The 65 high HLA matches in the data comprised 45 individuals (some individuals were matched with more than one). One individual was iteratively selected from these 45 as "recipient", and "donors" were randomly drawn until a high HLA match was encountered. This was repeated 10000 times. Consistent with the expectation from chance, an average of 65.35±37.5 donors had to be tested in order to identify a match. These procedures were then repeated, but rather than randomly drawing donors, they were drawn in rank order in accordance with their rapidly obtainable optimized olfactory fingerprint distance, starting with the closest. It was found that the average number of individuals that had to be tested in order to identify a match was 44±29, implying a 32% savings (t (64)=5.5, p<$10^{-6}$). In other words, using this brief perceptual test one could rank-order the population in order to save more than 30% of HLA tests.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bushdid C, Magnasco M O, Vosshall L B, & Keller A (2014) Humans candiscriminate more than 1 trillion olfactory stimuli. Science 343(6177):1370-1372.
2. Yeshurun Y & Sobel N (2010) An Odor is Not Worth a Thousand Words:From Multidimensional Odors to Unidimensional Odor Objects. *Annual Review of Psychology* 61:219-241.
3. Gilad Y & Lancet D (2003) Population differences in the human functional olfactory repertoire. *Mol Biol Evol* 20(3):307-314.
4. Keller A, Zhuang H, Chi Q, Vosshall L B, & Matsunami H (2007) Genetic variation in a human odorant receptor alters odour perception. *Nature* 449(7161):468-472.

5. Araneda R C, Kini A D, & Firestein S (2000) The molecular receptive range of an odorant receptor. *Nat Neurosci* 3(12):1248-1255.
6. Axel R (1995) The molecular logic of smell. *Sci Am* 273(4):154-159.
7. Buck L B (1996) Information coding in the vertebrate olfactory system. *Annu Rev Neurosci* 19:517-544.
8. Mainland J D, et al. (2013) The missense of smell: functional variability in the human odorant receptor repertoire. *Nat Neurosci* 17(1):114-120.
9. Menashe I, Man O, Lancet D, & Gilad Y (2003) Different noses for different people. *Nat Genet* 34(2):143-144.
10. Wandell B A (1995) *Foundations of vision* (Sinauer Associates).
11. Wysocki C J & Beauchamp G K (1984) Ability to smell androstenone is genetically determined. *Proc Natl Acad Sci USA* 81(15):4899-4902.
12. Menashe I, et al. (2007) Genetic elucidation of human hyperosmia to isovaleric acid. *PLoS Biol* 5(11):e284.
13. Amadou C, et al. (2003) Co-duplication of olfactory receptor and MHC class Igenes in the mouse major histocompatibility complex. *Human molecular genetics* 12(22):3025-3040.
14. Ziegler A, Dohr G, & Uchanska-Ziegler B (2002) Possible roles for products of polymorphic MHC and linked olfactory receptor genes during selection processes in reproduction. *Am J Reprod Immunol* 48(1):34-42.
15. Younger R M, et al. (2001) Characterization of clustered MHC-linked olfactory receptor genes in human and mouse. *Genome research* 11(4):519-530.
16. Jacob S, McClintock M K, Zelano B, & Ober C (2002) Paternally inherited HLA alleles are associated with women's choice of male odor. *Nat Genet* 30(2):175-179.
17. Wedekind C, Seebeck T, Bettens F, & Paepke A J (1995) MHC-dependent mate preferences in humans. *Proc Biol Sci* 260(1359):245-249.
18. Wedekind C & Penn D (2000) MHC genes, body odours, and odour preferences. *Nephrology, dialysis, transplantation: official publication of the European Dialysis and Transplant Association—European Renal Association* 15(9):1269-1271.
19. Milinski M & Wedekind C (2001) Evidence for MHC-correlated perfume preferences in humans. *Behav Ecol* 12(2):140-149.
20. Christakis N A & Fowler J H (2014) Friendship and natural selection. *Proc Natl Acad Sci USA* 111 Suppl 3:10796-10801.
21. Wise P, Olsson M, & Cain W (2000) Quantification of odor quality. *Chem Senses* 25(4):429-443.22. Khan R M, et al. (2007) Predicting odor pleasantness from odorant structure: pleasantness as a reflection of the physical world. *J Neurosci* 27(37):10015-10023.
23. Keller A, Hempstead M, Gomez I A, Gilbert A N, & Vosshall L B (2012) An olfactory demography of a diverse metropolitan population. *BMC Neurosci* 13:122.
24. Majid A & Burenhult N (2014) Odors are expressible in language, as long as you speak the right language. *Cognition* 130(2):266-270.
25. Dravnieks A (1982) Odor quality: semantically generated multidimensional profiles are stable. *Science* 218:799-801.
26. Schiffman S S (1974) Physicochemical correlates of olfactory quality. *Science* 185(146):112-117.
27. Anderson M J (2001) A new method for non!parametric multivariate analysis of variance. *Austral ecology* 26(1):32-46.
28. Stevens J C, Cain W S, & Burke R J (1988) Variability of Olfactory Thresholds. *Chemical Senses* 13(4):643-653.
29. Santoro S W & Dulac C (2012) The activity-dependent histone variant H2BE modulates the life span of olfactory neurons. *Elife* 1:e00070.
30. Cadiou H, et al. (2014) Postnatal Odorant Exposure Induces Peripheral Olfactory Plasticity at the Cellular Level. *The Journal of Neuroscience* 34(14):4857-4870.
31. Wang H W, Wysocki C J, & Gold G H (1993) Induction of olfactory receptor sensitivity in mice. *Science* 260 (5110):998-1000.
32. Yee K K & Wysocki C J (2001) Odorant exposure increases olfactory sensitivity: olfactory epithelium is implicated. *Physiol Behav* 72(5):705-711.
33. Brown R E, Singh P B, & Roser B (1987) The major histocompatibility complex and the chemosensory recognition of individuality in rats. *Physiol Behav* 40(1):65-73.
34. Freeman-Gallant C R, Meguerdichian M, Wheelwright N T, & Sollecito S V (2003) Social pairing and female mating fidelity predicted by restriction fragment length polymorphism similarity at the major histocompatibility complex in a songbird. *Molecular ecology* 12(11):3077-3083.
35. Reusch T B, Haberli M A, Aeschlimann P B, & Milinski M (2001) Female sticklebacks count alleles in a strategy of sexual selection explaining MHC polymorphism. *Nature* 414(6861):300-302.
36. Yamazaki K, et al. (1976) Control of mating preferences in mice by genes in the major histocompatibility complex. *The Journal of experimental medicine* 144(5):1324-1335.
37. McRae J F, et al. (2012) Genetic variation in the odorant receptor OR2J3 is associated with the ability to detect the "grassy" smelling odor, cis-3-hexen-1-ol. *Chem Senses* 37(7):585-593.
38. Kang N & Koo J (2012) Olfactory receptors in non-chemosensory tissues. *BMB Rep* 45(11):612-622.
39. Feldmesser E, et al. (2006) Widespread ectopic expression of olfactory receptor genes. *BMC Genomics* 7:121.
40. Busse D, et al. (2014) A Synthetic Sandalwood Odorant Induces Wound Healing Processes in Human Keratinocytes via the Olfactory Receptor OR2AT4. *Journal of Investigative Dermatology*.
41. Pinto J M, Wroblewski K E, Kern D W, Schumm L P, & McClintock M K (2014) Olfactory dysfunction predicts 5-year mortality in older adults. *PLoS One* 9(10):e107541.
42. Frasnelli J & Hummel T (2005) Olfactory dysfunction and daily life. *Eur Arch Otorhinolaryngol* 262(3):231-235.
43. Doty R L, et al. (1991) Olfactory dysfunction in three neurodegenerative diseases. *Geriatrics* 46 Suppl 1:47-51.
44. Perricone C, et al. (2013) Smell and autoimmunity: a comprehensive review. *Clin Rev Allergy Immunol* 45(1):87-96.

What is claimed is:

1. A method of determining olfactory perception signature of a subject, the method comprising:
providing the subject with a plurality of physical odorant samples for sniffing;
for each sniffed odorant sample, presenting to the subject, by a user interface, a set of odorant descriptors and a respective set of rating controls, and receiving ratings entered by the subject using said rating controls, each rating being indicative of a descriptiveness of a respective odorant descriptor for said odorant sample, thereby obtaining a set of descriptiveness levels for said odorant sample; and calculating, by a computer, relations between pairs of sets of descriptiveness levels corresponding to pairs of odorant samples, to provide a vector of relations, said vector representing the olfactory perception signature of the subject;

wherein the method comprises obtaining an olfactory perception signature of another subject and comparing said olfactory perception signature of the subject with said olfactory perception signature of the other subject, and, based on said comparison, determining likelihood for Human leukocyte antigen (HLA) matching between the subject and said other subject.

2. The method of claim 1, wherein said calculation of said relations comprises, for each pair of odorant samples, averaging squared differences between descriptiveness levels of a first odorant sample of said pair, and respective descriptiveness levels of a second odorant sample of said pair.

3. The method of claim 1, further comprising generating a graphical output describing said vector of relations.

4. The method of claim 1, wherein said obtaining comprises accessing a computer readable database and selecting said olfactory perception signature of said other subject from said database.

5. The method of claim 1, further comprising, based on said comparison, determining likelihood for successful relationship between the subject and said other subject.

6. The method of claim 1, wherein said comparison is by a metric selected from the group consisting of statistical correlation, Euclidian distance, Log-Euclidean distance, Angular distance, significance test distance, Chebyshev distance, Manhattan distance, and Minkowski distance.

7. The method of claim 1, further comprising:
accessing a computer readable database, each entry of said database having a database olfactory perception signature and annotation information;
searching said database for a database olfactory perception signature that is similar to said olfactory perception signature of the subject; and
extracting from the database annotation information associated with said similar database olfactory perception signature.

8. The method of claim 7, wherein each annotation information of said database is a personality trait, and the method comprises determining a psychological condition of the subject based on said extracted annotation information.

9. The method of claim 7, wherein each of at least some annotation information of said database is selected from the group consisting of: openness to experience, conscientiousness, extraversion, agreeableness, and neuroticism.

10. The method of claim 7, further comprising predicting an outcome of a psychological test for the subject, based on said extracted annotation information.

11. The method of claim 1, wherein said computer is remote from said user interface, and the method comprising transmitting said set of descriptiveness levels over a communication network to said computer.

12. A method for matching members of an online community, the method comprising:
providing to a member of the community a plurality of physical odorant samples for sniffing;
at a client computer: receiving sniffing ratings entered by the member using rating controls of a user interface of said client computer, calculating an olfactory perception signature of the member based on said ratings, and transmitting said olfactory perception signature to a server computer; and
at said server computer: accessing a computer readable database having a plurality of database olfactory perception signatures of other members of the community searching said database for a database olfactory perception signature that is similar to said olfactory perception signature of the member, and transmitting to said client computer an indication that a similar database olfactory perception signature has been found.

13. The method of claim 12, further comprising displaying on said user interface a set of odorant descriptors for each odorant sample, wherein said sniffing ratings are indicative of descriptiveness of each odorant descriptor of said set.

14. The method of claim 13, wherein said calculating said olfactory perception signature comprises calculating relations between pairs of sets of descriptiveness levels corresponding to pairs of odorant samples.

15. The method of claim 13, wherein said calculation of said relations comprises, for each pair of odorant samples, averaging squared differences between descriptiveness levels of a first odorant sample of said pair, and respective descriptiveness levels of a second odorant sample of said pair.

16. A server system for communicating in a matching service for matching members of an online community, the server system comprising:
a transceiver arranged to receive and transmit information on a communication network; and
a processor arranged to communicate with the transceiver, and perform code instructions, comprising:
code instructions for receiving from a client computer an olfactory perception signature of a member;
code instructions for accessing a computer readable database having a plurality of database olfactory perception signatures of other members of the community;
code instructions for searching said database for a database olfactory perception signature of another member of the community, wherein said database olfactory perception signature is similar to said olfactory perception signature of the member, and determining likelihood for Human leukocyte antigen (HLA) matching between the member and another member said other subject; and
code instructions for transmitting said likelihood to said client computer.

17. A client system for communicating in a matching service for matching members of an online community, the client system comprising:
a transceiver arranged to receive and transmit information on a communication network; and
a processor arranged to communicate with the transceiver, and perform code instructions, comprising:
code instructions for displaying a set of rating controls on a user interface;
code instructions for receiving sniffing ratings entered by a member using said rating controls;
code instructions for calculating an olfactory perception signature of the member based on said ratings;
code instructions for transmitting said olfactory perception signature to a server computer; and
code instructions for receiving from said server computer a likelihood for Human leukocyte antigen (HLA) matching between the member and a matching member that has been found in a database, based on said transmitted olfactory perception signature.

18. The system of claim 17, wherein said processor is arranged to display on said user interface a set of odorant descriptors, respectively corresponding to said set of rating controls, wherein said sniffing ratings are descriptiveness levels corresponding to said odorant descriptors.

19. The system of claim 18, wherein said processor is arranged to display said set of odorant descriptors and said a set of rating controls a plurality of times, and to receive said sniffing ratings a respective plurality of times, thereby to obtain a plurality of sets of descriptiveness levels, wherein said calculating said olfactory perception signature comprises calculating relations between pairs of sets of descriptiveness levels.

20. The system of claim 19, wherein said calculation of said relations comprises, for each pair of sets, averaging squared differences between descriptiveness levels of a first set pair, and respective descriptiveness levels of a second set of said pair.

21. A method of determining olfactory perception signature of a subject, the method comprising:
    providing the subject with a plurality of physical odorant samples for sniffing;
    for each sniffed odorant sample, presenting to the subject, by a user interface, a set of odorant descriptors and a respective set of rating controls, and receiving ratings entered by the subject using said rating controls, each rating being indicative of a descriptiveness of a respective odorant descriptor for said odorant sample, thereby obtaining a set of descriptiveness levels for said odorant sample; and
    calculating, by a computer, relations between pairs of sets of descriptiveness levels corresponding to pairs of odorant samples, to provide a vector of relations, said vector representing the olfactory perception signature of the subject;
    wherein the method comprises:
    accessing a computer readable database, each entry of said database having a database olfactory perception signature and annotation information, wherein each annotation information of said database is a personality trait;
    searching said database for a database olfactory perception signature that is similar to said olfactory perception signature of the subject;
    extracting from the database annotation information associated with said similar database olfactory perception signature; and
    determining a psychological condition of the subject based on said extracted annotation information.

22. A method of determining olfactory perception signature of a subject, the method comprising:
    providing the subject with a plurality of physical odorant samples for sniffing;
    for each sniffed odorant sample, presenting to the subject, by a user interface, a set of odorant descriptors and a respective set of rating controls, and receiving ratings entered by the subject using said rating controls, each rating being indicative of a descriptiveness of a respective odorant descriptor for said odorant sample, thereby obtaining a set of descriptiveness levels for said odorant sample; and
    calculating, by a computer, relations between pairs of sets of descriptiveness levels corresponding to pairs of odorant samples, to provide a vector of relations, said vector representing the olfactory perception signature of the subject;
    wherein the method comprises:
    accessing a computer readable database, each entry of said database having a database olfactory perception signature and annotation information, wherein each of at least some annotation information of said database is selected from the group consisting of: openness to experience, conscientiousness, extraversion, agreeableness, and neuroticism;
    searching said database for a database olfactory perception signature that is similar to said olfactory perception signature of the subject; and
    extracting from the database annotation information associated with said similar database olfactory perception signature.

23. A method of determining olfactory perception signature of a subject, the method comprising:
    providing the subject with a plurality of physical odorant samples for sniffing;
    for each sniffed odorant sample, presenting to the subject, by a user interface, a set of odorant descriptors and a respective set of rating controls, and receiving ratings entered by the subject using said rating controls, each rating being indicative of a descriptiveness of a respective odorant descriptor for said odorant sample, thereby obtaining a set of descriptiveness levels for said odorant sample; and
    calculating, by a computer, relations between pairs of sets of descriptiveness levels corresponding to pairs of odorant samples, to provide a vector of relations, said vector representing the olfactory perception signature of the subject;
    wherein the method comprises:
    accessing a computer readable database, each entry of said database having a database olfactory perception signature and annotation information;
    searching said database for a database olfactory perception signature that is similar to said olfactory perception signature of the subject;
    extracting from the database annotation information associated with said similar database olfactory perception signature; and
    predicting an outcome of a psychological test for the subject, based on said extracted annotation information.

* * * * *

UNITED STATES PATENT AND TRADEMARK OFFICE
CERTIFICATE OF CORRECTION

PATENT NO. : 10,204,176 B2
APPLICATION NO. : 15/188104
DATED : February 12, 2019
INVENTOR(S) : Noam Sobel et al.

It is certified that error appears in the above-identified patent and that said Letters Patent is hereby corrected as shown below:

On the Title Page

Item (72) Inventors:
Line 2, "Rohovot" should be changed to --Rehovot--
Line 4, "Rohovot" should be changed to --Rehovot--

Signed and Sealed this
Thirtieth Day of April, 2019

Andrei Iancu
*Director of the United States Patent and Trademark Office*